United States Patent [19]
Karpeisky et al.

[11] Patent Number: 6,159,951
[45] Date of Patent: Dec. 12, 2000

[54] 2'-O-AMINO-CONTAINING NUCLEOSIDE ANALOGS AND POLYNUCLEOTIDES

[75] Inventors: Alexander Karpeisky, Lafayette; Leonid Beigelman, Longmont, both of Colo.

[73] Assignee: Ribozyme Pharmaceuticals Inc., Boulder, Colo.

[21] Appl. No.: 08/982,841

[22] Filed: Dec. 2, 1997

Related U.S. Application Data

[60] Provisional application No. 60/037,998, Feb. 13, 1997.

[51] Int. Cl.$^7$ ............................. A61K 31/70; C07H 19/04
[52] U.S. Cl. ............................... 514/45; 514/46; 514/47; 514/48; 514/49; 514/50; 514/51; 536/26.26; 536/26.6; 536/26.7; 536/26.74; 536/27.21; 536/27.6; 536/27.8; 536/27.81; 536/28.1; 536/28.5; 536/28.53; 536/28.54; 536/23.1
[58] Field of Search ............................... 536/26.26, 26.6, 536/26.7, 26.74, 27.21, 276, 17.8, 27.81, 28.1, 28.5, 28.53, 28.54, 23.1; 935/33, 34, 69.1; 435/6, 91.1, 172.1, 240, 240.2, 375, 325; 514/44, 43, 45, 46, 47, 48, 49, 50, 51

[56] References Cited

U.S. PATENT DOCUMENTS

| | | |
|---|---|---|
| 4,987,071 | 1/1991 | Cech et al. . |
| 5,334,711 | 8/1994 | Sproat et al. . |
| 5,783,425 | 7/1998 | Dudycz et al. .......................... 536/23.1 |

FOREIGN PATENT DOCUMENTS

| | | |
|---|---|---|
| 0 360 257 | 9/1989 | European Pat. Off. . |
| 91/03162 | 3/1991 | WIPO . |
| 92/07065 | 4/1992 | WIPO . |
| 93/15187 | 8/1993 | WIPO . |
| 93/23569 | 11/1993 | WIPO . |
| 94/02595 | 2/1994 | WIPO . |
| 95/13378 | 5/1995 | WIPO . |
| 95/23225 | 8/1995 | WIPO . |
| 96/22689 | 8/1996 | WIPO . |

OTHER PUBLICATIONS

Mohr et al., "A tyrosyl–tRNA synthetase can function similarly to an RNA structure in the Tetrahymena ribozyme," *Nature* 370:147–150 (1994).

Michel and Westhof, "Slippery substratrates," *Nat. Struct. Biol.* 1:5–7 (1994).

Lisacek et al., "Automatic Identification of Group I Intron Cores in Genomic DNA Sequences," *J. Mol. Biol.* 235:1206–1217 (1994).

Herschlag and Cech, "Catalysis of RNA Cleavage by the *Tetrahymena thermophila* Ribozyme 1. Kinetic Description of the Reaction of an RNA Substrate Complementary to the Active Site," *Biochemistry* 29:10159–10171 (1990).

Herschlag and Cech, "Catalysis of RNA Cleavage by the *Tetrahymena thermophila* Ribozyme. 2. Kinetic Description of the Reaction of an RNA Substrate That Forms a Mismatch at the Active Site," *Biochemistry* 29:10172–10180 (1990).

Knitt et al., "ph Dependencies of the Tetrahymena Ribozyme Reveal an Unconvential Origin of an Apparent $pK_a$," *Biochemistry* 35:1560–1570 (1996).

Bevilacqua et al., "A Mechanistic Framework for the Second Step of Splicing Catalyzed by the Tetrahymena Ribozyme," *Biochemistry* 35:648–568 (1996).

Li et al., "Thermodynamic and Activation Parameters for Binding of a Pyrene–Labeled Substrate by the Tetrahymena Ribozyme: Docking is Not Diffusion–Controlled and is Driven by a Favorable Entropy Change," *Biochemistry* 34:14394–14399 (1995).

Banerjee and Turner, "The Time Dependence of Chemical Modification Reveals Slow Steps in the Folding of a Group I Ribozyme," *Biochemistry* 34:6504–6512 (1995).

Zarrinkar and Williamson, "The P9.1–P9.2 peripheral extension helps guide folding of the Tetrahymena ribozyme," *Nucleic Acids Research* 24:854–858 (1996).

Strobel et al., "Minor Groove Recognition of the Conserved G·U Pair at the Tetrahymena Ribozyme Reaction Site," *Science* 267:675–679 (1995).

Strobel et al., "Exocyclic Amine of the Conserved G·U Pair at the Cleavage Site of the Tetrahymena Ribozyme Contributes to 5'–Splice Site Selection and Transition State Stabilization," *Biochemistry* 35:1201–1211 (1996).

Sullenger and Cech, "Ribozyme–mediated repair of defective mRNA by targeted trans–splicing," *Nature* 371:619–622 (1994).

Robertson et al., "Purification and Properties of a Specific *Escherichia coli* Ribonuclease which Cleaves a Tyrosine Transfer Ribonucleic Acid Precursor", *J. Biol. Chem.* 247:5243–5251 (1972).

Yuan et al., "Targeted cleavage of mRNA by human RNase P," *Proc. Natl. Acad. Sci. USA* 89:8006–8010 (1992).

Harris et al., "Identification of phosphates involved in catalysis by the ribozyme RNase P RNA," *RNA* 1:210–218 (1995).

Pan et al., "Probing of tertiary interactions in RNA: 2'–Hydroxyl–base contacts between the Rnase P and pre–tRNA," *Proc. Natl. Acad. Sci. USA* 92:12510–12514 (1995).

Pyle et al., "Building a Kinetic Framework for Group II Intron Ribozyme Activity: Quantitation of Interdomain Binding and Reaction Rate," *Biochemistry* 33:2716–2725 (1994).

Michels and Pyle, "Conversion of a Group II Intron into a New Multiple–Turnover Ribozyme that Selectively Cleaves Oligonucleotides: Elucidation of Reaction Mechanism and Structure/Function Relationships," *Biochemistry* 34:2965–2977 (1995).

Zimmerly et al., "A Group II Intron RNA is a Catalytic Component of a DNA Endonuclease Involved in Intron Mobility," *Cell* 83:529–538 (1995).

(List continued on next page.)

*Primary Examiner*—James O. Wilson
*Attorney, Agent, or Firm*—McDonnell Boehnen Hulbert & Berghoff

[57] ABSTRACT

Novel nucleoside or nucleotide analogs comprising 2'-O-amino residues, processes for their synthesis and incorporation into polynucleotides.

18 Claims, 10 Drawing Sheets

OTHER PUBLICATIONS

Michel et al., "Structure and Activities of Group II Introns," *Annu. Rev. Biochem.* 64:435–461 (1995).

Abramovitz et al., "Catalytic Role of 2'-Hydroxyl Groups Within a Group II Intron Active Site," *Science* 271:1410–1413 (1996).

Daniels et al., "Two Competing Pathways for Self–splicing Group II Introns: A Quantitative Analysis of in Vitro Reaction Rates and Products," *J. Mol. Biol.* 256:31–49 (1996).

Hampel et al., "'Hairpin' Catalytic RNA Model: Evidence for Helices and Sequence Requirement for Substrate RNA," *Nucleic Acids Research* 18:299–304 (1990).

Chowrira et al., "Novel guanosine requirement for catalysis by the hairpin ribozyme," *Nature* 354:320–322 (1991).

Berzal–Herranz et al., "Essential nucleotide sequences and secondary structure elements of the hairpin ribozyme," *EBMO J.* 12:2567–2574 (1993).

Joseph et al., "Substrate selection rules for the hairpin ribozyme determined by in vitro selection, mutation, and analysis of mismatched substrates," *Genes & Development* 7:130–138 (1993).

Berzal–Herranz et al., "In vitro selection of active hairpin ribozymes by sequential RNA–catalyzed cleavage and ligation reactions," *Genes & Development* 6:129–134 (1992).

Hegg et al., "Kinetics and Thermodynamics of Intermolecular Catalysis by Hairpin Ribozymes," *Biochemistry* 34:15813–15828 (1995).

Grasby et al., "Purine Functional Groups in Essential Residues of the Hairpin Ribozyme Required for Catalytic Cleavage of RNA," *Biochemistry* 34:4068–4076 (1995).

Schmidt et al., "Base and sugar requirements for RNA cleavage of essential nucleoside residues in internal hoop B of the hairpin ribozyme: implications for secondary structure," Nucleic Acids Research 24:573–581 (1996).

Perrotta and Been, "A pseudoknot–like structure required for efficeint self–cleavage of hepatitis delta virus RNA," *Nature* 350:434–436 (1991).

Puttaraju et al., "A circular trans–acting hepatitis delta virus ribozyme," *Nucleic Acids Research* 21:4253–4258 (1993).

Sandler and Karo, *Organic Functional Group Preparation*, vol. III, edited by Wasserman, Academic Press, Inc., pp. 378–523 (1989).

Uhlenbeck, "A Small Catalytic Oligoribonucleotide," *Nature* 328:596–600 (1987).

Hansske et al, "Recent Aspects of the Chemistry of Nucleosides, Nucleotides and Nucleic Acids," *Tetrahedron* 40:125 (1984).

Beaucage et al., "The Chemical Synthesis of DNA/RNA" *Bioorganic Chemistry :Nucleic Acids* 2, 36–74 (1996).

Brown et al., "Modern Machine–aided Methods of Oligodeoxyribonucleotide synthesis" *Oligonucleorides and Analogues: A Practical Approach* 1–23 (1991).

Burgess et al., "Synthesis of an Oxyamide Linked Nucleotide Dimer and Incorporation into Antisense Oligonucleotide Sequences" *J. Chem. Soc. Chem. Commun.* 915–916 (1994).

Cech, "Ribozymes and Their Medical Implications" *JAMA* 260(20) 3030–3034 (1988).

Chowrira et al, "Extensive Phosphorothioate Substitution Yields Highly and Nuclease–resistant Hairpin Ribozymes" *Nucl. Acid Res.* 20(11) 2835–2840 (1992).

Christoffersen et al., "Ribozymes as Human Therapeutic Agents" *J. of Medicinal Chem.* 38(12) 2023–2037 (1995).

Collins et al., "Reaction Conditions and Kinetics of Self–Clevage of a Ribozyme Derived from Neurospora VS RNA" *Biochem* 32, 2795–2799 (1993).

Duval–Valentin et al., "Specific Inhibition of Transcription by Triple Helix–forming Oligonucleotides" *Proc. Natl. Acad. Sci. USA* 89, 504–508 (1992).

Eaton et al., "Ribonucleosides and RNA" *Annu. Rev. Biochem.* 64, 837–863 (1995).

Egholm et al., "PNA Hybridizes to complementary Oligonucleotides Obeying the Watson–Crick Hydrogen–bonding Rules" *Nature* 365, 566–568 (1993).

Feldstein et al., "Two Sequences Participating in sathe Autolytic Processing of Satellite Tobacco Ringspot Virus Complementary RNA" *Gene* 82, 53–61 (1989).

Forster et al., "External Guide Sequences for an RNA Enzyme" *Science* 783–786 (1990).

Grasby et al., "Application of Synthetic Oligoribonucleotide Analogues in Studies of RNA Structure and Function" *Proc. Indian Acad. Sci.* 106(5) 1003–1022 (1994).

Griffin Jr. et al., "Group II Intron Ribozymes that Cleave DNA and RNA Linkages with Similar Efficiency, and Lack Contacts with Substrate 2'–hydroxyl Groups" *Chem. & Biol.* 2(11) 761–770 (1995).

Growchowski et al., "A New Synthesis of O–aAlkylhydroxylamines" *Synthesis* 682–684 (1976).

Growchowski et al., "The Synthesis of N–Glycosyloxyphthaliomides via Mitsunobu Reaction" *Bulletin of the Polish Acad of Sci. Chem.* 35(7/8) 255–260 (1987).

Grochowski et al., "A New Class of Monosaccharide Derivatives: O–phthalimidohexoses" *Carbohydrate Research* C15–16 (1976).

Guerrier–Takada et al., "The RNA Moiety of Ribonuclease P is the Catalytic Subunit of the Enzyme" *Cell* 35, 849–857 (1983).

Guo et al., "Efficient Trans–Clevage of a Stem—loop RNA Substrate by a Ribozyme Derived from Neurospora VS RNA" *EMBO J.* 14(2) 368–376 (1995).

Hall, *The Modified Nucleosides in Nucleic Acids* Columbia Univ. Press (1991) (Table of contents only).

Hampel et al., "RNA Catalytic Properties of the Minumum (–)s TRSV Sequence" *Biochem.* 28, 4929–4933 (1989).

Hampel et al., "'Hairpin' Catalytic RNA Model: Evidence for Helices and Sequence Requirement for Substrate RNA" *Nucl. Acid Res.* 18(2) 299–304 (1990).

Haseloff et al., "Simple RNA Enzymes with New and Highly Specific Endoribonuclease Activities" *Nature* 334, 585–591(1988).

Hertel et al., "Numbering System for the Hammerhead" *Nucl. Acid. Res.* 20(12) 3252 (1992).

Hutchinson et al., "The Synthesis, Reactions and Properties of Nucleoside Mono–, Di–, Tri–, and Tetraphosphates and Nucleotides with Changes in the Phosphoryl Residue" *Chem of Nucleosides and Nucleotides* 2, 81–160 (1991).

Jeffries et al., "A Catalytic 13–mer Ribozyme" *Nucl. Acid Res.* 17(4) 1371–1377 (1989).

Kim et al., "Three–dimensional Model of the Active Site of the Self–splicing rRNA Precursor of Tetrahymena" *Proc. Natl. Acad. Sci. USA* 84, 8788–8792 (1987).

Kondo et al., "Synthesis of 5'(3')–O–Amino Nucleosides" *Nucl. Acid Res* 16, 93–96 (1985).

Li et al., "Cleavage of RNase P of Gene N mRNA Reduces Bacteriophage λ Bust Size" *Nucl. Acid Res.* 24(5) 835–842 (1996).

Limbach et al., "Summary: The Modified Nucleosides of RNA" *Nucl. Acid Res.* 22(12) 2183–2196 (1994).

Michels Jr. et al., "Conversion of a Group II Intron into a New Multiple–Turnover Ribozyme that Selectively Cleaves Oligonucleotides: Elucidation of Reaction Mechanism and Structure/Function Relationships" *Biochem* 34, 2965–2977 (1995).

Milligan et al., "Synthesis of Small RNAs Using T7 RNA Polymerase" *Methods in Enzymol.* 180, 51–62 (1989).

Mitsonubu, "The Use of Diethyl Azodicarboxylate and Triphenylphosphine in Synthesis and Transformation of Natural Products" *Synthesis* 1–28 (1981).

Nielsen et al., "DNA Analogues with Nonphosphodiester Backbones" *Ann. Rev. Biomol. Struct.* 24, 167–183 (1995).

Perbost et al., "Synthesis of 5'–O–Amino–2'–Deoxypyromidine and Purine Nucleoside: Building–Blocks for Antisense Oligonucleotides" *J.Org. Chem.* 60,5150–5156 (1995).

Perrault et al., "Mixed Deoxyribo– and Ribo–Oligonucleotides with Catalytic Activity" *Nature* 344, 565–567 (1990).

Perrotta et al., "Clevage of Oligoribonucleotides by a Ribozyme Derived from the Hepatitis δ Virus RNA Sequence" *Biochem.* 31, 16–21 (1992).

Pieken et al., "Kinetic Characterization of Ribonuclease–Resistant 2'–Modified Hammerhead Ribozymes" *Science* 253, 314–317 (1991).

Rossi et al., "Ribozymes as Anti–Hiv–1 Therapeutic Agents: Principles, Applications and Problems" *Aids Res. and Human Retroviruses* 8(2) 183–189 (1992).

Sandler et al., *Organic Functional Group Preparation* 2nd$^n$ ed. (Table of Contents Only).

Saville et al., "A Site–specific Self–clevage Reaction Performed by a Novel RNA in *Neurospora Mitochondria*" *Cell* 685–696 (1990).

Saville et al., "RNA–mediated Ligation of Self–Clevage Products of a Neurospora Mitchondrial Plasmid Transcript" *Proc. Natl. Acad Sci. USA* 88, 8826–8830 (1991).

Scaringe et al., "Chemical Synthesis of Biologically Active Oligoribonucleotides Using β–Cyanoethyl Protected Ribonucleoside Phosphoramidites" *Nucl. Acid Res.* 18(18) 5433–5441(1990).

Stein et al., "Antisense Oligonucleotides as Therapeutic Agents—Is the Bullet Really Magical?" *Science* 261, 1004–1012 (1993).

Torrence et al., "Targeting RNA for Degradation with (2'–5') Oligoadenylateantisense Chimera" *Proc. Natl. Acad.* 90, 1300–1304 (1993).

Tronchet et al., "136. Radicaux Libres Derives De Sucres. V$^{11}$Derives d'osamines N–hydroxylees et composes viosins" *Helv. Chim. Acta.* 65, 1404–1411 (1982).

Tronchet et al., "Some Protected O–amino Sugars and Their Derivatives" *Carbohydrate res.* 204, 145–156 (1990).

Tronchet et al., "Novel Types of Bicyclonucleosides: Isoxazolidinofuranosylthymines" *Nucleosides & Nucleotides* 13(10) 2071–2079 (1994).

Tuschl et al., "Importance of Exocyclic Base Functional Groups of Central Core Guanosines for Hammerhead Ribozyme Activity" *Biochem.* 32, 11658–11668 (1993).

Uhlmann et al., "Antisense Oligonucleotides: A New Therapeutics Principle" *Chem. Rev.* 90(4) 544–584 (1990).

Usman et al., "Automated Chemical Synthesis of Long Oligoribonucleotides Using 2'–O–Silylated Ribonucleoside 3'–O–Phorphoramidites on a Controlled–pore Glass support: Synthesis of a 43–Nucleotide Sequence Similar to the 3'–Half Molecule of an *Escherichia Coli* Formylmethionine tRNA" *J. Am.Chem. Soc.* 109(25) 7845–7854 (1987).

Usman et al., "Chapter 30. Catalytic RNA (Ribozymes) as Drugs" *Annual Reports in Med. Chem.* 30, 285–293 (1995).

Usman et al., "Exploiting the Chemical Synthesis of RNA" *TIBS* 17, 334–339(1992).

Vasseur et al., "Oligonucleosides: Synthesis of a Novel Methylhydroxylamine–Linked Nucleoside Dimer and Its Incorporation into Antisense Sequences" *J. Am. Chem. Soc.* 114, 4006–4007 (1992).

Wincott et al., "Synthesis, Deprotection, Analysis and Purification of RNA and Ribozymes" *Nucl. Acid. Res.* 23(14) 2677–2684 (1995).

Zaug et al., "The Tetrahymena Ribozyme Acts like an RNA Restriction Endonuclease" *Nature* 324, 429–433 (1986).

HAMMERHEAD RIBOZYME SUBSTRATE MOTIFS

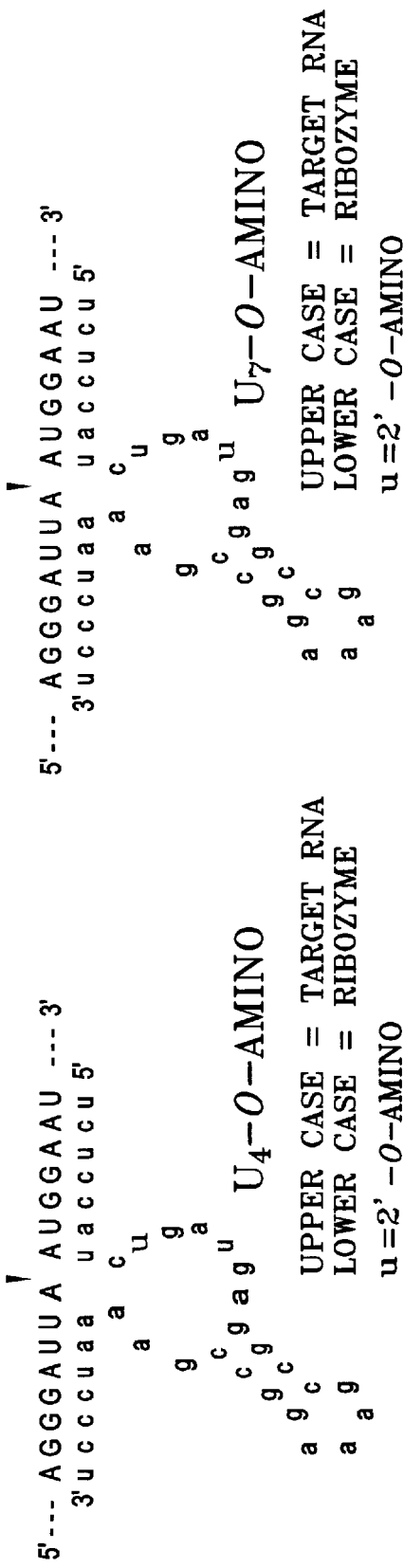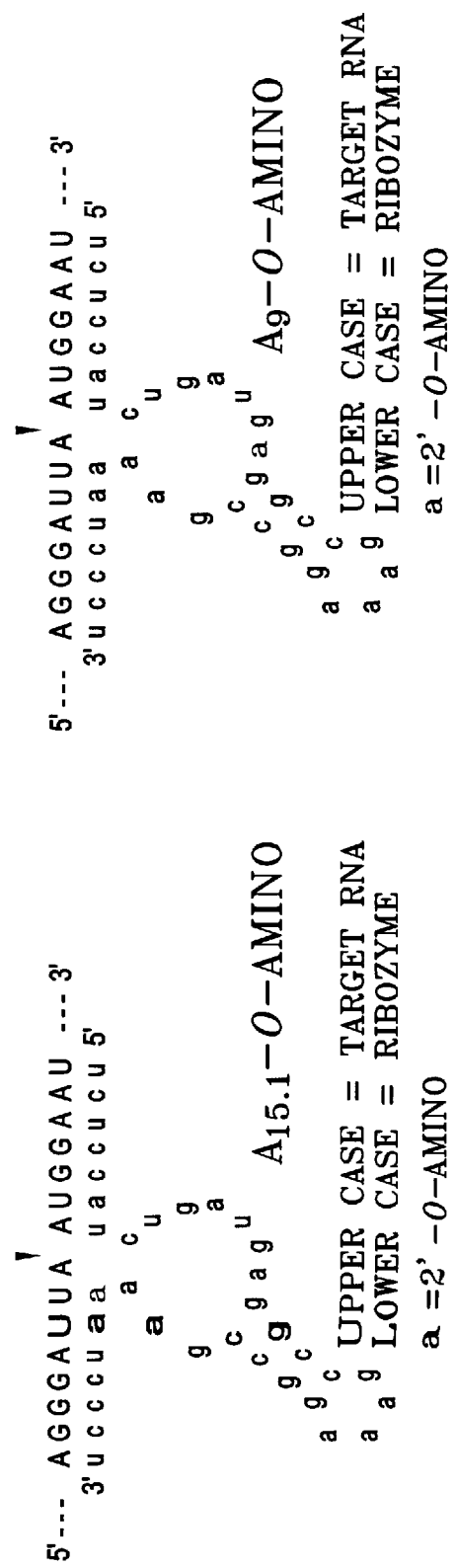
FIG. 9A

RNA CLEAVAGE BY 2'-O-AMINO-SUBSTITUTED RIBOZYMES

| RIBOZYMES | $k_{obs}$ (min$^{-1}$) |
|---|---|
| ALL RNA | 0.7 |
| U4-O-AMINO | 0.007 |
| U7-O-AMINO | 0.72 |
| A15.1-O-AMINO | 0.006 |
| A9-O-AMINO | 0.5 |

FIG. 9B

2'-O-AMINO-CONTAINING NUCLEOSIDE ANALOGS AND POLYNUCLEOTIDES

CROSS-REFERENCE TO RELATED APPLICATIONS

This application claims the benefit of Alexander Karpeisky et al, U.S. Provisional Application 60/037,998, entitled "2'-O-Amino-Containing Nucleoside Analogs and Polynucleotides", filed Feb. 13, 1997, which is hereby incorporated herein by reference in its entirety, including any drawings and figures.

BACKGROUND OF THE INVENTION

This invention relates to novel nucleoside or nucleotide analogs, processes for their synthesis and incorporation into polynucleotides.

The following is a brief description of nucleoside analogs. This summary is not meant to be complete but is provided only for an understanding of the invention that follows. This summary is not an admission that all of the work described below is prior art to the claimed invention.

Nucleoside modifications of bases and sugars, have been discovered in a variety of naturally occurring RNA (e.g., tRNA, mRNA, rRNA; reviewed by Hall, 1971 *The Modified Nucleosides in Nucleic Acids,* Columbia University Press, New York; Limbach et al., 1994 *Nucleic Acids Res.* 22, 2183). In an attempt to understand the biological significance, structural and thermodynamic properties, and nuclease resistance of these nucleoside modifications in nucleic acids, several investigators have chemically synthesized nucleosides, nucleotides and phosphoramidites with various base and sugar modifications and incorporated them into oligonucleotides.

Uhlmann and Peyman, 1990, *Chem. Reviews* 90, 543, review the use of certain nucleoside modifications to stabilize antisense oligonucleotides.

Usman et al., International PCT Publication Nos. WO/93/15187; and WO 95/13378; describe the use of sugar, base and backbone modifications to enhance the nuclease stability of enzymatic nucleic acid molecules.

Eckstein et al., International PCT Publication No. WO 92/07065 describe the use of sugar, base and backbone modifications to enhance the nuclease stability of enzymatic nucleic acid molecules.

Grasby et al., 1994, *Proc. Indian Acad. Sci.,* 106, 1003, review the "applications of synthetic oligoribonucleotide analogues in studies of RNA structure and function".

Eaton and Pieken, 1995, *Annu. Rev. Biochem.,* 64, 837, review sugar, base and backbone modifications that enhance the nuclease stability of RNA molecules Mitsunobu, 1981, *Synthesis,* 1, 1–28, described a process for the conversion of alcohol (ROH) to aminooxy alcohol ($RONH_2$).

The process descibed by Mitsunobu (supra) has been been applied in the conversion of sugars and disaccharides (Grochowski et al., 1976, 50, C15; *Synthesis* 1976, 682; *J. Bull. Pol. Acad. Sci. Chem. Commun.,* 1987, 35, 255; Tronchet et al., 1982, *Helv. Chim. Acta.,* 65, 1404; *Carbohydr. Res.,* 1990, 204).

The process descibed by Mitsunobu (supra) has also been applied in the synthesis of 3'-O—$3NH_2$ nucleosides and 5'-O—$NH_2$ nucleosides (Nielsen, 1995, *Annu. Rev. Biomol. Struc.,* 24, 167; Burgess et al., 1994, J. Chem. Soc. Chem. Commun., 915; Kondo et al., 1985, *Am. Chem. Soc. Symp. Ser.,* 16, 93; Vasseur et al., 1992, *J. Am. Chem. Soc.,* 114, 4006; Tronchet et al., 1994, 13, 2071; Perbost et al., 1995, *J. Org. Chem.,* 60, 5150).

The references cited above are distinct from the presently claimed invention since they do not disclose and/or contemplate the synthesis of the nucleoside analogs, such as the 2'-O-amino nucleosides of the instant invention.

SUMMARY OF THE INVENTION

This invention relates to a nucleoside or a nucleotide comprising a nucleic acid sugar portion, wherein the 2' position of the sugar has the formula: 2'-O—$NHR_1$, wherein $R_1$ is independently H, aminoacyl group, peptidyl group, biotinyl group, cholesteryl group, lipoic acid residue, retinoic acid residue, folic acid residue, ascorbic acid residue, nicotinic acid residue, 6-aminopenicillanic acid residue, 7-aminocephalosporanic acid residue, alkyl, alkenyl, alkynyl, aryl, alkylaryl, carbocyclic aryl, heterocyclic aryl, amide or ester. The invention also relates to a nucleoside or a nucleotide comprising a nucleic acid sugar portion, wherein the 2' position of the sugar has the formula: 2'-O—N=$R_3$, wherein $R_3$ is independently pyridoxal residue, pyridoxal-5-phosphate residue, 13-cis-retinal residue, 9-cis-retinal residue, alkyl, alkenyl, alkynyl, alkylaryl, carbocyclic alkylaryl, or heterocyclic alkylaryl.

This invention relates to novel nucleoside analogs having the Formula I:

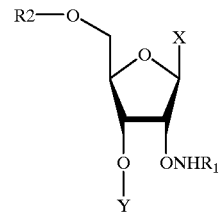

wherein, $R_1$ is independently H, aminoacyl group, peptidyl group, biotinyl group, cholesteryl group, lipoic acid residue, retinoic acid residue, folic acid residue, ascorbic acid residue, nicotinic acid residue, 6-arninopenicillanic acid residue, 7-aminocephalosporanic acid residue, alkyl, alkenyl, alkynyl, aryl, alkylaryl, carbocyclic aryl, heterocyclic aryl, amide or ester; X is independently a nucleotide base or its analog or hydrogen; Y is independently a phosphorus-containing group; and R2 is independently a blocking group or a phosphorus-containing group.

In a preferred embodiment the invention features novel nucleoside analogs having the Formula II:

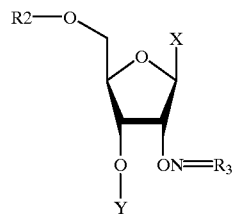

wherein, $R_3$ is independently pyridoxal residue, pyridoxal-5-phosphate residue, 13-cis-retinal residue, 9-cis-retinal residue, alkyl, alkenyl, alkynyl, alkylaryl, carbocyclic alkylaryl, or heterocyclic alkylaryl; X is independently a nucleotide base or its analog or hydrogen; Y is independently a phosphorus-containing group; and R2 is independently a blocking group or a phosphorus-containing group.

Specifically, an "alkyl" group refers to a saturated aliphatic hydrocarbon, including straight-chain, branched-chain, and cyclic alkyl groups. Preferably, the alkyl group has 1 to 12 carbons. More preferably it is a lower alkyl of from 1 to 7 carbons, more preferably 1 to 4 carbons. The alkyl group may be substituted or unsubstituted. When substituted the substituted group(s) is preferably, hydroxy, cyano, alkoxy, $NO_2$ or $N(CH_3)_2$, amino, or SH.

The term "alkenyl" group refers to unsaturated hydrocarbon groups containing at least one carbon-carbon double bond, including straight-chain, branched-chain, and cyclic groups. Preferably, the alkenyl group has 1 to 12 carbons. More preferably it is a lower alkenyl of from 1 to 7 carbons, more preferably 1 to 4 carbons. The alkenyl group may be substituted or unsubstituted. When substituted the substituted group(s) is preferably, hydroxyl, cyano, alkoxy, $NO_2$, halogen, $N(CH_3)_2$, amino, or SH.

The term "alkynyl" refers to an unsaturated hydrocarbon group containing at least one carbon-carbon triple bond, including straight-chain, branched-chain, and cyclic groups. Preferably, the alkynyl group has 1 to 12 carbons. More preferably it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, =O, =S, $NO_2$ or $N(CH_3)_2$, amino or SH.

An "aryl" group refers to an aromatic group which has at least one ring having a conjugated $\pi$ electron system and includes carbocyclic aryl, heterocyclic aryl and biaryl groups, all of which may be optionally substituted. The preferred substituent(s) on aryl groups are halogen, trihalomethyl, hydroxyl, SH, cyano, alkoxy, alkyl, alkenyl, alkynyl, and amino groups.

An "alkylaryl" group refers to an alkyl group (as described above) covalently joined to an aryl group (as described above).

"Carbocyclic aryl" groups are groups wherein the ring atoms on the aromatic ring are all carbon atoms. The carbon atoms are optionally substituted.

"Heterocyclic aryl" groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, pyrrolo, pyrimidyl, pyrazinyl, imidazolyl and the like, all optionally substituted.

An "amide" refers to an —C(O)—NH—R, where R is either alkyl, aryl, alkylaryl or hydrogen.

An "ester" refers to an —C(O)—OR', where R is either alkyl, aryl, or alkylaryl.

A "blocking group" is a group which is able to be removed after polynucleotide synthesis and/or which is compatible with solid phase polynucleotide synthesis.

A "phosphorus containing group" can include phosphorus in forms such as dithioates, phosphoramidites and/or as part of an oligonucleotide.

In a preferred embodiment, the invention features a process for synthesis of novel nucleoside analogs of formula I and/or Formula II.

In yet another preferred embodiment, the invention features the incorporation of novel nucleoside analogs of Formula I, Formula II or combinations thereof, into polynucleotides. These novel nucleoside analogs can be incorporated into polynucleotides enzymatically. For example by using bacteriophage T7 RNA polymerase, these novel nucleoside analogs can be incorporated into RNA at one or more positions (Milligan et al., 1989, *Methods Enzymol.*, 180, 51). Alternatively, novel nucleoside analogs can be incorporated into polynucleotides using solid phase synthesis (Brown and Brown, 1991, in *Oligonucleotides and Analogues: A Practical Approach*, p. 1, ed. F. Eckstein, Oxford University Press, New York; Wincoft et al., 1995, *Nucleic Acids Res.*, 23, 2677; Beaucage & Caruthers, 1996, in *Bioorganic Chemistry: Nucleic Acids*, p 36, ed. S. M. Hecht, Oxford University Press, New York).

The novel nucleoside analogs of Formula I, Formula II or combinations thereof, can be used for chemical synthesis of nucleotides, nucleotide-tri-phosphates and/or phosphoramidites as building blocks for selective incorporation into oligonucleotides. These oligonucleotides can be used as an antisense molecule, 2–5A antisense chimera, triplex forming oligonucleotides (TFO) or as an enzymatic nucleic acid molecule. The oligonucleotides can also be used as probes or primers for synthesis and/or sequencing of RNA or DNA.

Nucleosides of the instant invention can be readily converted into nucleotides, nucleotide diphosphate and nucleotide triphosphates using standard protocols (for a review see Hutchinson, 1991, in *Chemistry of Nucleosides and Nucleotides*, v.2, pp 81–160, Ed. L. B. Townsend, Plenum Press, New York, USA; incorporated by reference herein).

The novel nucleoside analogs of Formula I, Formula II or combinations thereof, can also be independently or in combination used as an antiviral, anticancer or an antitumor agent. These compounds can also be independently or in combination used with other antiviral, anticancer or an antitumor agents.

By "antisense" it is meant a non-enzymatic nucleic acid molecule that binds to target RNA by means of RNA-RNA or RNA-DNA or RNA-PNA (protein nucleic acid; Egholm et al., 1993 *Nature* 365, 566) interactions and alters the activity of the target RNA (for a review see Stein and Cheng, 1993 *Science* 261, 1004).

By "2–5A antisense chimera" it is meant, an antisense oligonucleotide containing a 5' phosphorylated 2'–5'-linked adenylate residues. These chimeras bind to target RNA in a sequence-specific manner and activate a cellular 2–5A-dependent ribonuclease which, in turn, cleaves the target RNA (Torrence et al., 1993 *Proc. Natl. Acad. Sci. USA* 90, 1300).

By "triplex forming oligonucleotides (TFO)" it is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504).

By "enzymatic nucleic acid" it is meant a nucleic acid molecule capable of catalyzing reactions including, but not limited to, site-specific cleavage and/or ligation of other nucleic acid molecules, cleavage of peptide and amide bonds, and trans-splicing.

The enzymatic nucleic acid is able to intramolecularly or intermolecularly cleave RNA or DNA and thereby inactivate a target RNA or DNA molecule. The enzymatic nucleic acid molecule that has complementarity in a substrate binding region to a specified gene target, also has an enzymatic activity that specifically cleaves RNA or DNA in that target. This complementarity functions to allow sufficient hybridization of the enzymatic RNA molecule to the target RNA or DNA to allow the cleavage to occur. 100% Complementarity is preferred, but complementarity as low as 50–75% may also be useful in this invention. The nucleic acids may be modified at the base, sugar, and/or phosphate groups.

The term enzymatic nucleic acid is used interchangeably with phrases such as ribozymes, catalytic RNA, enzymatic RNA, catalytic DNA, nucleozyme, DNAzyme, RNA enzyme, endoribonuclease, minizyme, leadzyme oligozyme, or DNA enzyme.

By "complementarity" is meant a nucleic acid that can form hydrogen bond(s) with other RNA sequence by either traditional Watson-Crick or other non-traditional types (for example, Hoogsteen type) of base-paired interactions.

Nucleic acid molecules having an endonuclease enzymatic activity are able to repeatedly cleave other separate RNA molecules in a nucleotide base sequence-specific manner. Such enzymatic RNA molecules can be targeted to virtually any RNA transcript, and efficient cleavage achieved in vitro (Zaug et al., 324, Nature 429 1986; Kim et al., 84 *Proc. Natl. Acad. Sci. USA* 8788, 1987; Haseloff and Gerlach, 334 *Nature* 585, 1988; Cech, 260 *JAMA* 3030, 1988; and Jefferies et al., 17 *Nucleic Acids Research* 1371, 1989).

Because of their sequence-specificity, trans-cleaving ribozymes show promise as therapeutic agents for human disease (Usman & McSwiggen, 1995 *Ann. Rep. Med. Chem.* 30, 285–294; Christoffersen and Marr, 1995 *J. Med. Chem.* 38, 2023–2037). Ribozymes can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

Seven basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base-pairing. Thus, it is thought that the specificity of action of a ribozyme is greater than that of antisense oligonucleotide binding the same RNA site.

In one of the preferred embodiments of the inventions herein, the enzymatic nucleic acid molecule is formed in a hammerhead or hairpin motif, but may also be formed in the motif of a hepatitis δ virus, group I intron, group II intron or RNaseP RNA (in association with an RNA guide sequence) or Neurospora VS RNA. Examples of such hammerhead motifs are described by Dreyfus, supra, Rossi et al., 1992, *AIDS Research and Human Retroviruses* 8, 183; of hairpin motifs by Hampel et al., EP0360257, Hampel and Tritz, 1989 *Biochemistry* 28, 4929, Feldstein et al., 1989, *Gene* 82, 53, Haseloff and Gerlach, 1989, *Gene*, 82, 43, and Hampel et al., 1990 *Nucleic Acids Res.* 18, 299; of the hepatitis δ virus motif is described by Perrotta and Been, 1992 *Biochemistry* 31, 16; of the RNaseP motif by Guerrier-Takada et al., 1983 *Cell* 35, 849; Forster and Altman, 1990, *Science* 249, 783; Li and Altman, 1996, *Nucleic Acids Res.* 24, 835; Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799; Guo and Collins, 1995, *EMBO. J.* 14, 363); Group II introns are described by Griffin et al., 1995, *Chem. Biol.* 2, 761; Michels and Pyle, 1995, *Biochemistry* 34, 2965; Pyle et al., International PCT Publication No. WO 96/22689; and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

Synthesis of nucleic acids greater than 100 nucleotides in length is difficult using automated methods, and the therapeutic cost of such molecules is prohibitive. In this invention, small nucleic acid motifs (e.g., antisense oligonucleotides, hammerhead or the hairpin ribozymes) are used for exogenous delivery. The simple structure of these molecules increases the ability of the nucleic acid to invade targeted regions of the mRNA structure.

The novel nucleoside analogs of the instant invention and/or the polynucleotides comprising these analogs are added directly to a cell, or can be complexed with cationic lipids, packaged within liposomes, or otherwise delivered to target cells. The nucleosides, nucleic acid or nucleic acid complexes can be locally administered to relevant tissues ex vivo, or in vivo through injection, infusion pump or stent, with or without their incorporation in biopolymers.

By "enzymatic portion" is meant that part of the ribozyme essential for cleavage of an RNA substrate.

By "substrate binding arm" is meant that portion of a ribozyme which is complementary to (i.e., able to base-pair with) a portion of its substrate. Generally, such complementarity is 100%, but can be less if desired. For example, as few as 10 bases out of 14 may be base-paired. Such arms are shown generally in FIGS. 1–3 as discussed below. That is, these arms contain sequences within a ribozyme which are intended to bring ribozyme and target RNA together through complementary base-pairing interactions; e.g., ribozyme sequences within stems I and III of a standard hammerhead ribozyme make up the substrate-binding domain (see FIG. 1).

By "oligonucleotide" or "polynucleotide" as used herein, is meant a molecule comprising two or more nucleotides.

By "unmodified nucleoside" is meant one of the bases adenine, cytosine, guanine, uracil joined to the 1' carbon of β-ribo-furanose.

By "modified nucleoside" is meant any nucleotide base which contains a modification in the chemical structure of an unmodified nucleotide base, sugar and/or phosphate.

Oligonucleotide conjugates with different types of biologically interesting macromolecules or reporter groups are useful as experimental tools. In this invention, the existence of a 2'-O-amino functionality facilitates formation of such conjugates. A majority of the methods known in the art for the chemical synthesis of such conjugates are based either on post-synthetic attachment of the molecule of interest to the 3'- and/or 5'-end of oligonucleotides using an appropriate spacer, or incorporation of the sugar, base and/or backbone-modified, monomeric nucleoside units into oligonucleotides during chemical synthesis. However, these methods have several disadvantages such as low yields and tedious synthesis schemes. To avoid these problems it is useful to use unique functional groups both in the oligonucleotides and in the molecule to be attached. These functional groups should be able to react quantitatively, under mild conditions and preferably in water solution. The main idea here is to design a nucleoside monomeric unit (phosphoramidite) bearing a unique functional group, which can be further used as a tether for conjugating any molecule of interest.

Formation of oximes (interaction of aldehydes or ketones with hydroxylamines) or oxyamides (interaction of carboxylic acids with hydroxylamines) are the organic reactions of choice which will meet the above requirements (Sandier, S. R.; Karo, W *Organic Functional Group Preparation* vol. III, ed. Wasserman H. H., Academic Press, Inc., 1989, pp 378–523).

In a preferred embodiment, an oligonucleotide would bear one or more hydroxylamino functionalities attached directly to the monomeric unit or through the use of an appropriate spacer (e.g., an alkyl moiety or any moiety which does not significantly interfere with the action of the nucleotide or the hydroxylamine functionality). Since oligonucleotides have neither aldehyde nor hydroxylamino groups, the formation of an oxime would occur selectively using oligo as a polymeric template. This approach would facilitate the attachment of practically any molecule of interest (peptides, polyamines, coenzymes, oligosaccharides, lipids, etc.) directly to the oligonucleotide using either aldehyde or carboxylic function in the molecule of interest.

Scheme 1. Post synthetic Oxime Bond Formation

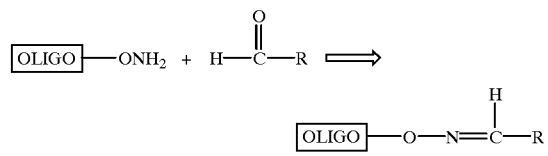

Scheme 2. Chemical Ligation of Oligonucleotides

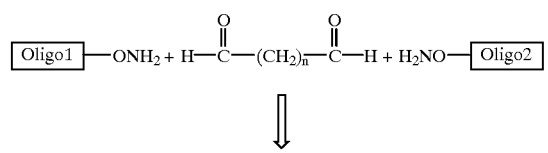

-continued

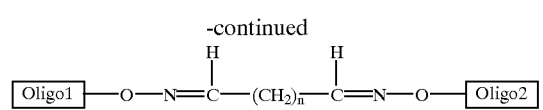

Advantages of oxime bond formation:

The oximation reaction proceeds in water
Quantitative yields
Hydrolytic stability in a wide pH range (5–8)
The amphoteric nature of oximes allows them to act either as weak acids or weak bases.
Oximes exhibit a great tendency to complex with metal ions In yet another preferred embodiment, the aminooxy "tether" in oligonucleotides, such as a ribozyme, is reacted with different compounds bearing carboxylic groups (e.g. aminoacids, peptides, "cap" structures ,etc.) resulting in the formation of oxyamides as shown below.

Scheme 3. Post synthetic oxyamide bond formation

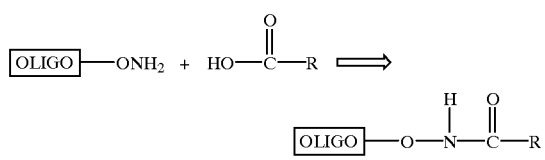

In a preferred embodiment the invention features a process for the synthesis of a 2'-O-amino nucleoside, such as 2'-O-amino adenosine, 2'-O-amino guanosine, 2'-O-amino cytidine, 2'-O-amino uridine and others, comprising the steps of: a) contacting a 3' and 5'-protected arabino nucleoside with a sulfonylating reagent, such as tri-fluoromethane sulfonic anhydride, tri-fluoromethane sulfonic chloride and others, under conditions suitable for the formation of 3' and 5'-protected 2'-arabino sulfonyl nucleoside; b) displacement of the sulfonyl group from the 2'-arabino sulfonyl nucleoside with N-hydroxy-phthalimide in the presence of a strong organic base, such as 1,8-diazabicyclo(5.4.0)undec-7-ene and the like, under conditions suitable for the formation of 3' and 5'-protected 2'-O-N-phthaloyl ribonucleoside; c) deprotection of the N-phthaloyl ribonucleoside with a fluoride containing reagent, such as tetrabutylammonium fluoride, triethylamine trihydrofluoride and the like, under conditions suitable for the formation of 2'-O-N-phthaloyl ribonucleoside; and d) contacting the 2'-O-N-phthaloyl ribonucleoside with a reagent selected from a group consisting of alkylamine (such as methylamine, ethylamine, butylamine and the like), hydrazine, N-phenyl hydrazine and N-alkylhydrazine (such as N-methylhydrazine and the like), under conditions suitable for the formation of said 2'-O-amino nucleoside.

Other features and advantages of the invention will be apparent from the following description of the preferred embodiments thereof, and from the claims.

DESCRIPTION OF THE PREFERRED EMBODIMENTS

The drawings will first briefly be described.
Drawings

FIG. 1 is a diagrammatic representation of the hammerhead ribozyme domain known in the art. Stem II can be $\geq 2$ base-pair long. Each N is independently any base or non-nucleotide as used herein.

Figure 1:
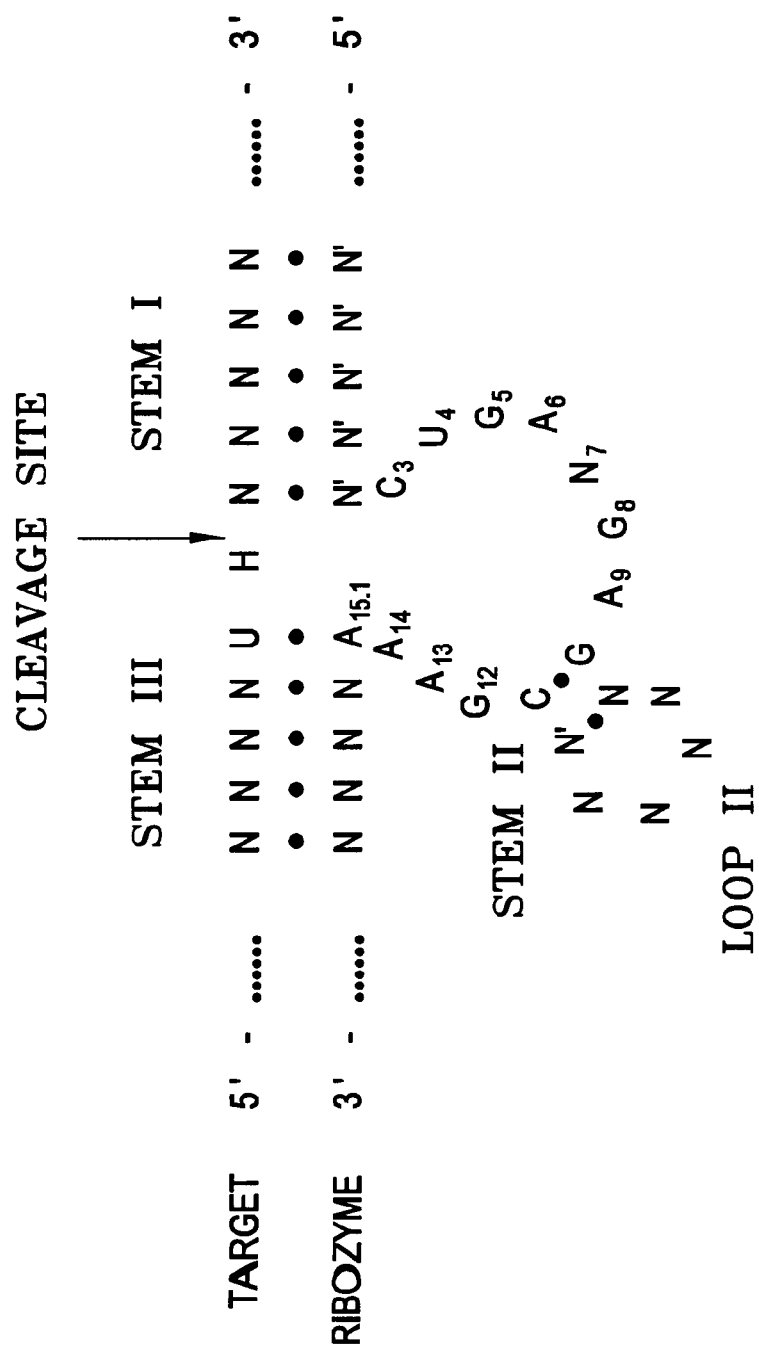
Figure 2A:
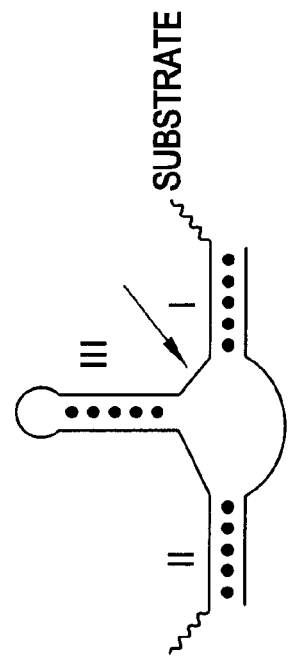
FIG. 2a is a diagrammatic representation of the hammerhead ribozyme domain known in the art.
Figure 2B:
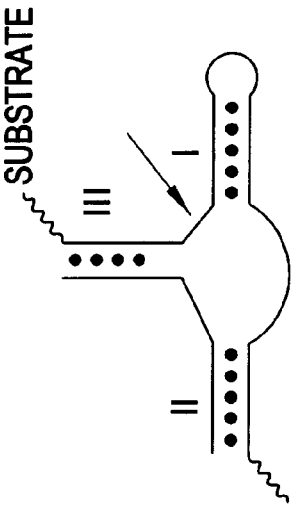
FIG. 2b is a diagrammatic representation of the hammerhead ribozyme as divided by Uhlenbeck (1987, *Nature*, 327, 596–600) into a substrate and enzyme portion.
Figure 2C:
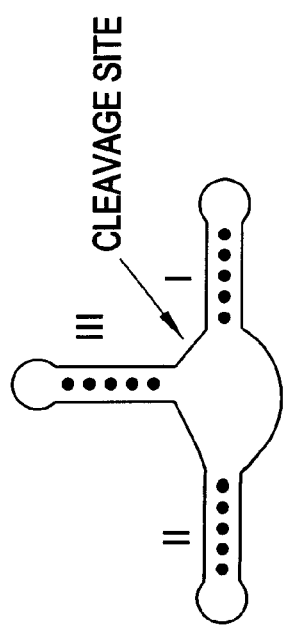
Figure 2D:
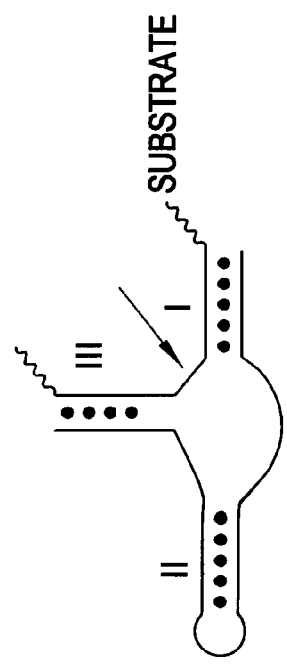

FIG. 2c is a similar diagram showing the hammerhead divided by Haseloff and Gerlach (1988, *Nature*, 334, 585–591) into two portions; and FIG. 2d is a similar diagram showing the hammerhead divided by Jeffries and Symons (1989, *Nucl. Acids. Res.*, 17, 1371–1371) into two portions.

Figure 3:
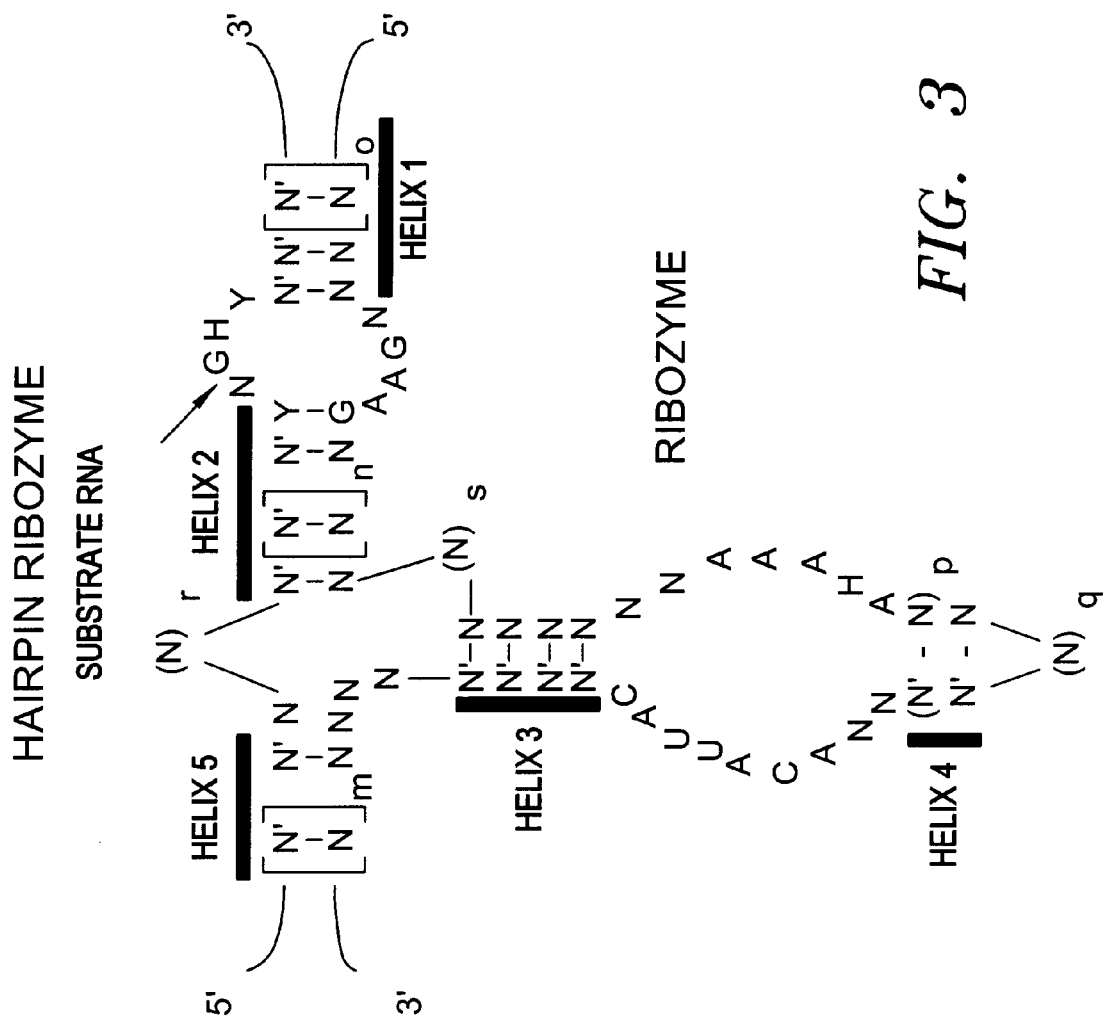

FIG. 3 is a diagrammatic representation of the general structure of a hairpin ribozyme. Helix 2 (H2) is provided with at least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq$1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq$2 bases. The connecting loop can also be replaced with a non-nucleotide linker molecule. H, refers to bases A, U or C. Y refers to pyrimidine bases. "-----" refers to a chemical bond.

Figure 4:
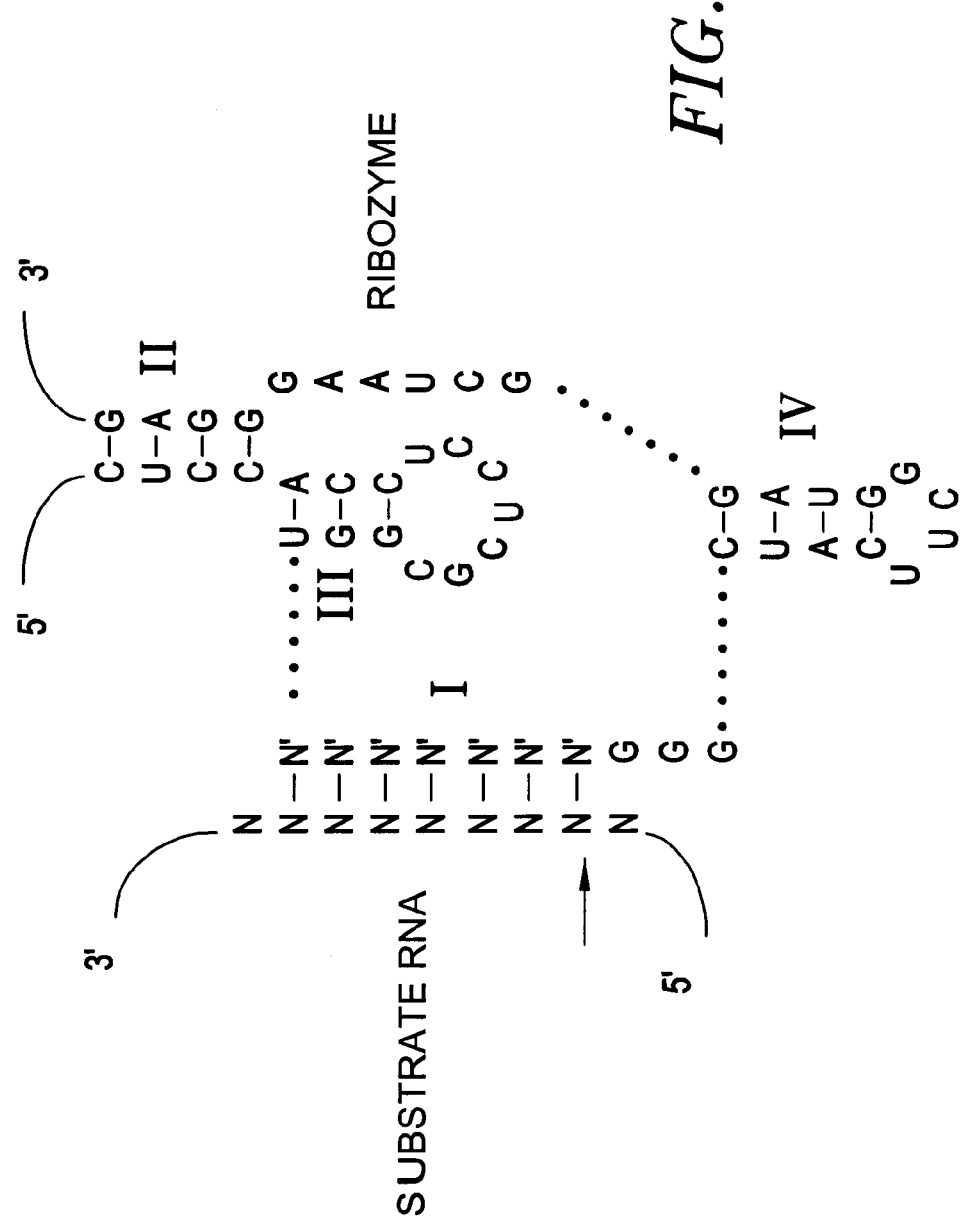

FIG. 4 is a representation of the general structure of the hepatitis delta virus ribozyme domain known in the art. Each N is independently any base or non-nucleotide as used herein.

Figure 5:
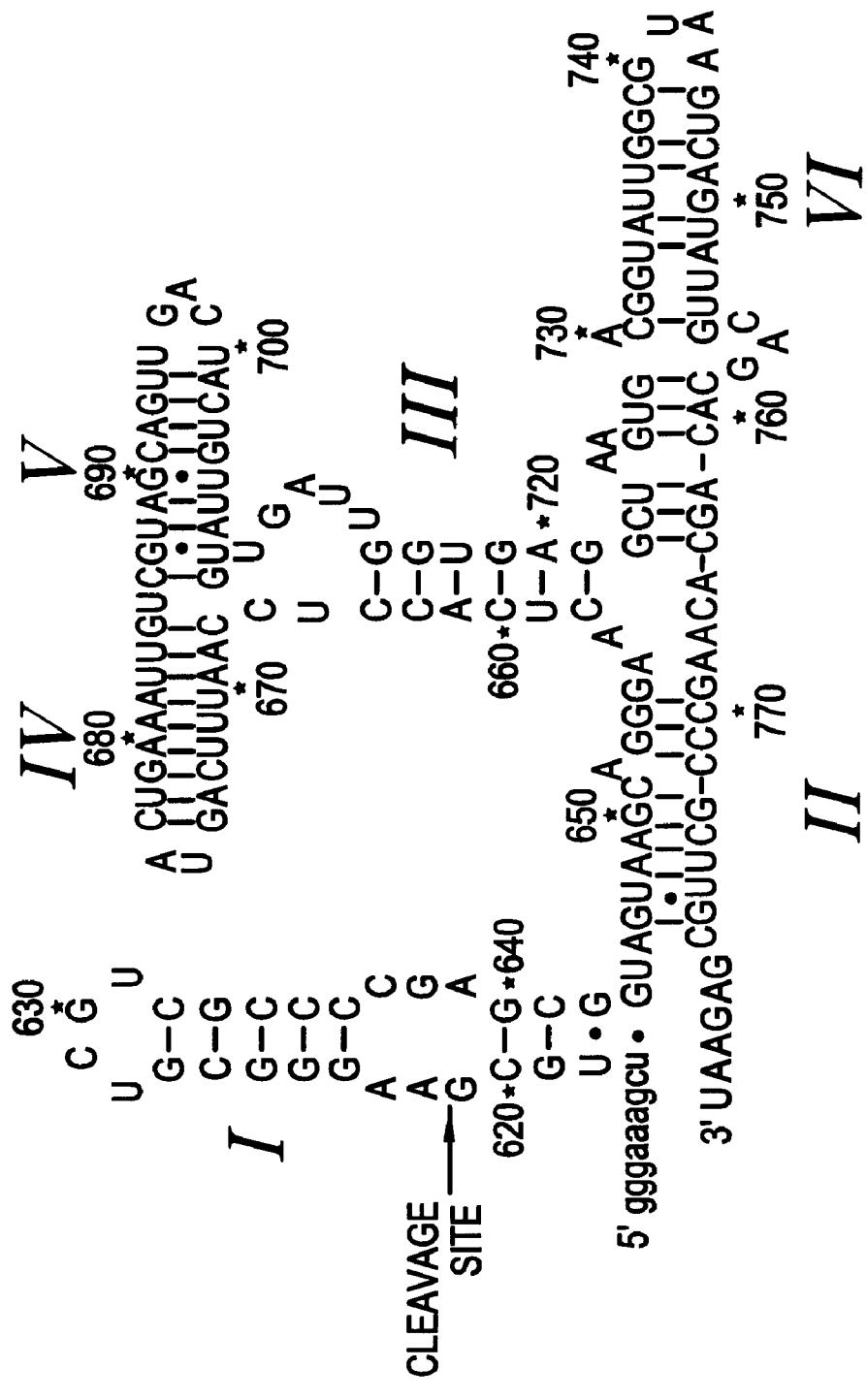

FIG. 5 is a representation of the general structure of the self-cleaving VS RNA ribozyme domain.

Figure 6:
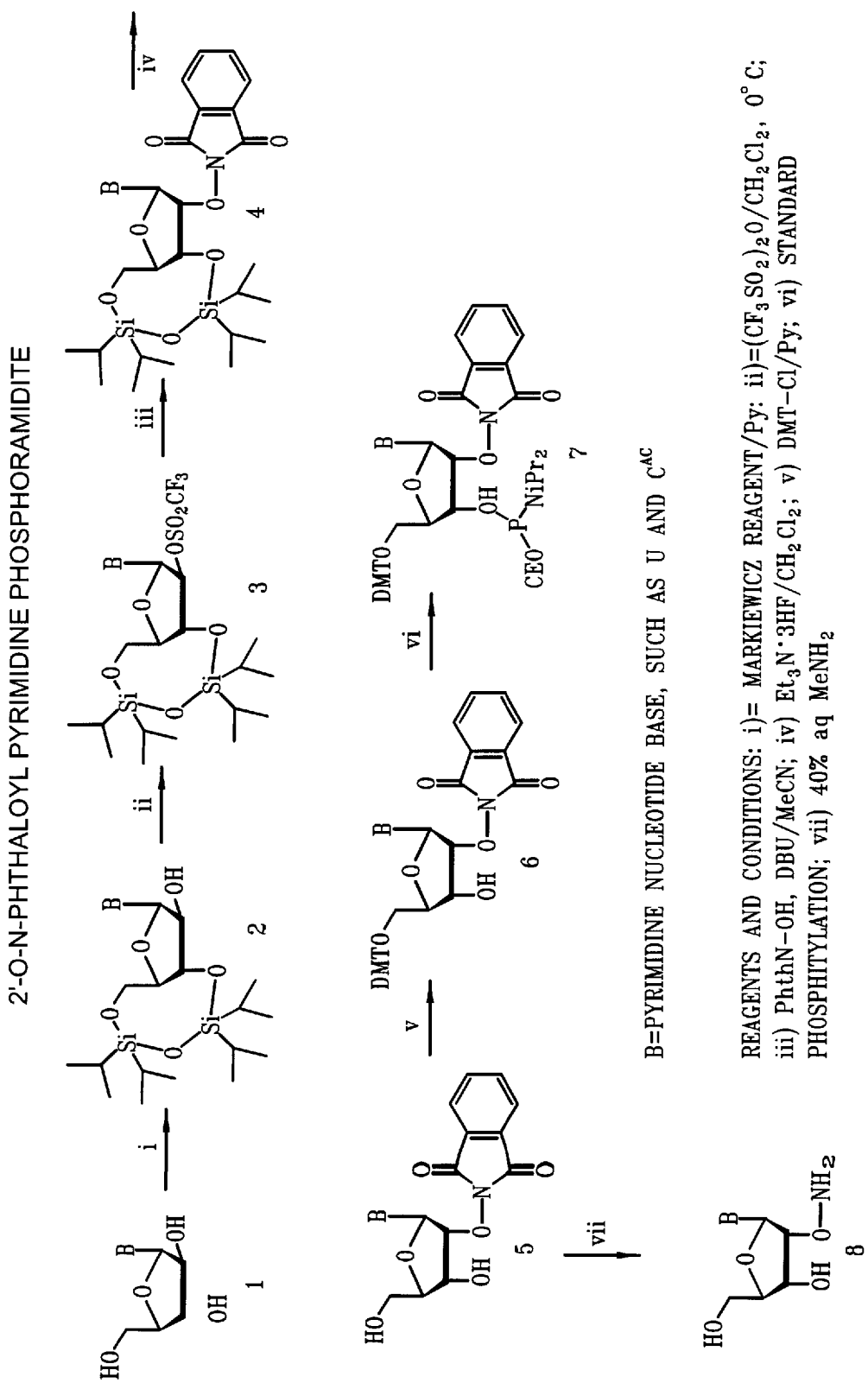

FIG. 6 is a scheme for the synthesis of 2'-O-amino pyrimidine nucleoside and phosphoramidite.

Figure 7:
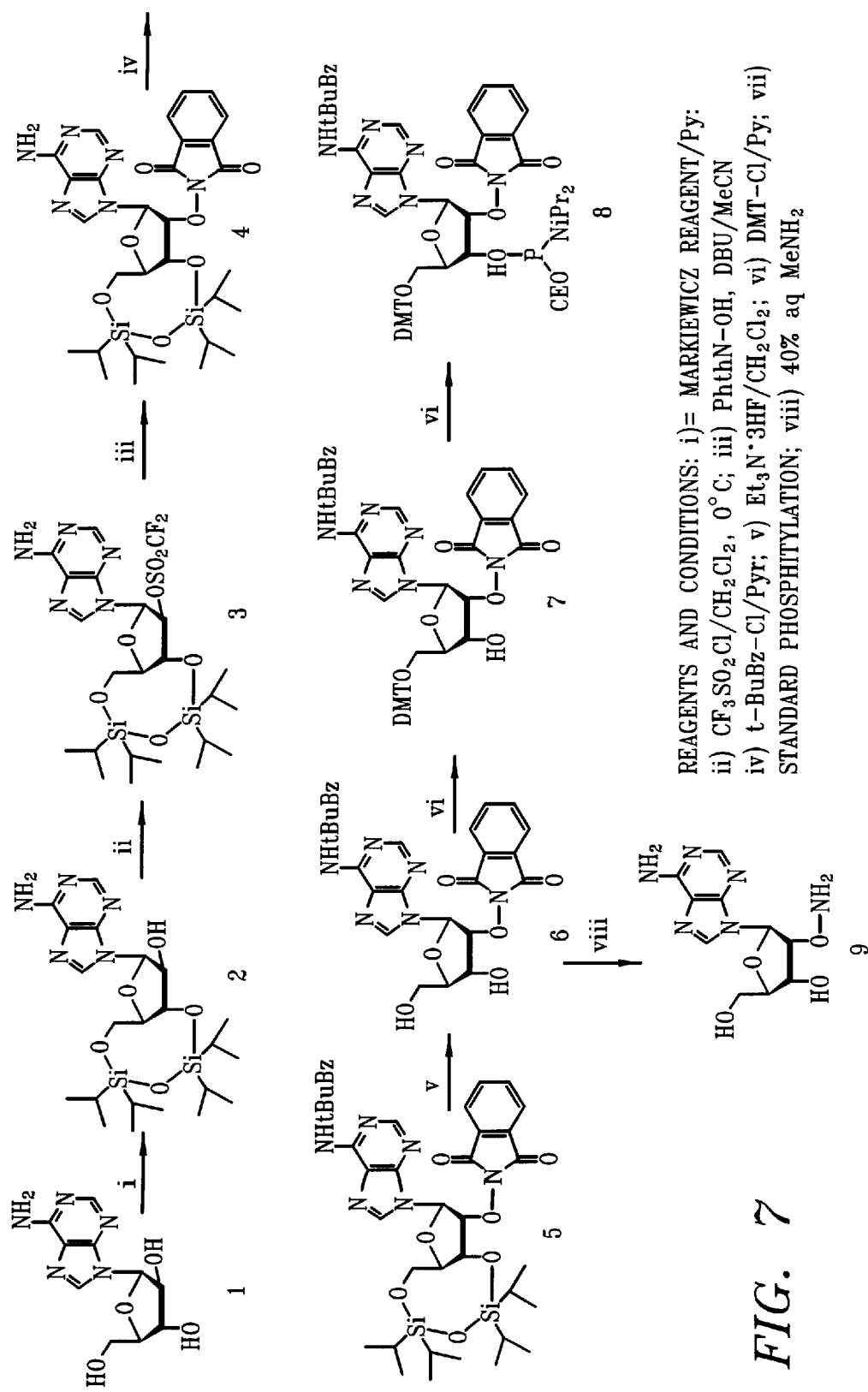

FIG. 7 is a scheme for the synthesis of 2'-O-amino adenosine nucleoside and phosphoramidite.

Figure 8:
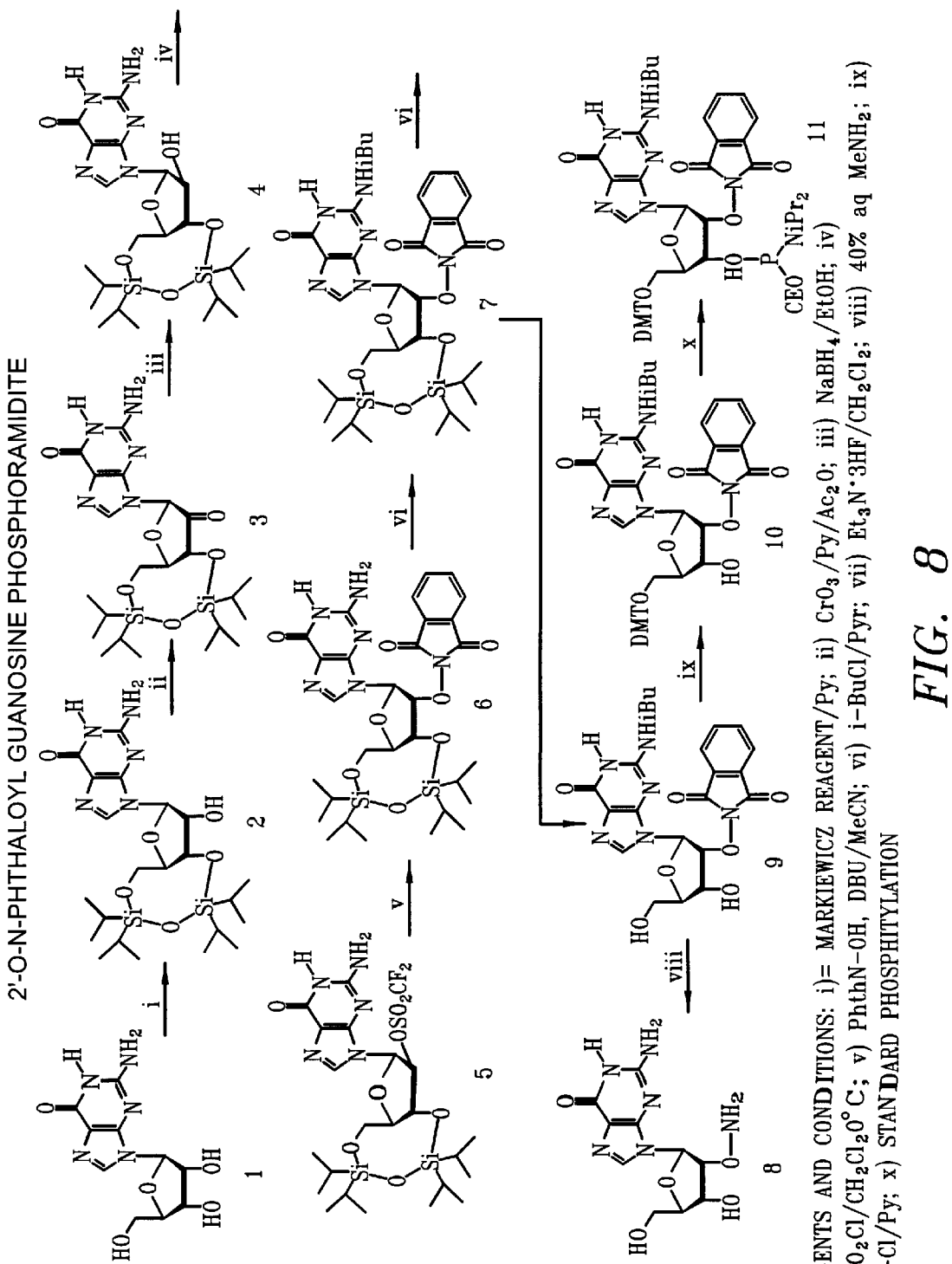

FIG. 8 is a scheme for the synthesis of 2'-O-amino guanosine nucleoside and phosphoramidite.

FIGS. 9A–B are a diagrammatic representation of hammerhead ribozymes substituted with 2'-O-amino groups at various positions (FIG. 9A) shows the rates of RNA cleavage reaction catalyzed by those ribozymes (FIG. 9B).

SYNTHESIS OF POLYNUCLEOTIDES

Synthesis of polynucleotides greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure.

RNA molecules, such as the ribozymes are chemically synthesized. The method of synthesis used follows the procedure for normal RNA synthesis as described in Usman et al., 1987 *J. Am. Chem. Soc.*, 109, 7845; Scaringe et al., 1990 *Nucleic Acids Res.*, 18, 5433; and Wincott et al., 1995 *Nucleic Acids Res.* 23, 2677–2684 and makes use of common nucleic acid protecting and coupling groups, such as dimethoxytrityl at the 5'-end, and phosphoramidites at the 3'-end. Small scale synthesis were conducted on a 394 Applied Biosystems, Inc. synthesizer using a modified 2.5 $\mu$mol scale protocol with a 5 min coupling step for alkylsilyl protected nucleotides and 2.5 min coupling step for 2'-O-methylated nucleotides. Table 2 outlines the amounts, and the contact times, of the reagents used in the synthesis cycle. A 6.5-fold excess (163 $\mu$L of 0.1 M=16.3 $\mu$mol) of phosphoramidite and a 24-fold excess of S-ethyl tetrazole (238 $\mu$L of 0.25 M=59.5 $\mu$mol) relative to polymer-bound 5'-hydroxyl was used in each coupling cycle. Average coupling yields on the 394 Applied Biosystems, Inc. synthesizer, determined by calorimetric quantitation of the trityl fractions, were 97.5–99%. Other oligonucleotide synthesis reagents for the 394 Applied Biosystems, Inc. synthesizer: detrylation solution was 2% TCA in methylene chloride (ABI); capping was performed with 16% N-methyl imidazole in THF (ABI) and 10% acetic anhydride/10% 2,6-lutidine in THF (ABI); oxidation solution was 16.9 mM $I_2$, 49 mM pyridine, 9% water in THF (Millipore). B & J Synthesis Grade acetonitrile was used directly from the reagent bottle. S-Ethyl tetrazole solution (0.25 M in acetonitrile) was made up from the solid obtained from American International Chemical, Inc.

Deprotection of the RNA was performed as follows. The polymer-bound oligoribonucleotide, trityl-off, was transferred from the synthesis column to a 4 mL glass screw top vial and suspended in a solution of methylamine (MA) at 65° C. for 10 min. After cooling to −20° C., the supernatant was removed from the polymer support. The support was washed three times with 1.0 mL of EtOH:MeCN:$H_2O$ 3:1:1, vortexed and the supernatant was then added to the first supernatant. The combined supernatants, containing the oligoribonucleotide, were dried to a white powder.

The base-deprotected oligoribonucleotide was resuspended in anhydrous TEA•HF/NMP solution (250 $\mu$L of a solution of 1.5 mL N-methylpyrrolidinone, 750 $\mu$L TEA and 1.0 mL TEA•3HF to provide a 1.4M HF concentration) and heated to 65° C. for 1.5 h. The resulting, fully deprotected, oligomer was quenched with 50 mM TEAB (9 mL) prior to anion exchange desalting.

For anion exchange desalting of the deprotected oligomer, the TEAB solution was loaded onto a Qiagen 500® anion exchange cartridge (Qiagen Inc.) that was prewashed with 50 mM TEAB (10 mL). After washing the loaded cartridge with 50 mM TEAB (10 mL), the RNA was eluted with 2 M TEAB (10 mL) and dried down to a white powder.

Inactive hammerhead ribozymes were synthesized by substituting a U for $G_5$ and a U for $A_{14}$ (numbering from (Hertel, K. J., et al., 1992, *Nucleic Acids Res.*, 20, 3252)).

The average stepwise coupling yields were >98% (Wincoft et al., 1995 *Nucleic Acids Res.* 23, 2677–2684).

Hairpin ribozymes are synthesized either as one part or in two parts and annealed to reconstruct the active ribozyme (Chowrira and Burke, 1992 *Nucleic Acids Res.*, 20, 2835–2840).

RNAs are purified by gel electrophoresis using general methods or are purified by high pressure liquid chromatography (HPLC; See Stinchcomb et al., International PCT Publication No. WO 95/23225, the totality of which is hereby incorporated herein by reference) and are resuspended in water.

Various modifications to ribozyme structure can be made to enhance the utility of ribozymes. Such modifications will enhance shelf-life, half-life in vitro, stability, and ease of introduction of such ribozymes to the target site, e.g., to enhance penetration of cellular membranes, and confer the ability to recognize and bind to targeted cells.

Optimizing Ribozyme Activity

Ribozyme activity can be optimized as described by Stinchcomb et al., supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; Rossi et al., International Publication No. WO 91/03162; as well as Sproat, U.S. Pat. No. 5,334,711 which describe various chemical modifications that can be made to the sugar moieties of enzymatic RNA molecules). Modifications which enhance their efficacy in cells, and removal of stem II bases to shorten RNA synthesis times and reduce chemical requirements are desired. (All these publications are hereby incorporated by reference herein).

Administration of Ribozyme

Sullivan et al., PCT WO 94/02595, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., PCT WO93/23569 which have been incorporated by reference herein.

EXAMPLES

The following are non-limiting examples showing the synthesis and activity of the certain compounds of Formula I of the instant invention and polynucleotides comprising one or more of these compounds. Those in the art will recognize that certain reaction conditions such as temperatures, pH, ionic conditions, reaction times and solvent conditions described in the following examples are not meant to be limiting and can be readily modified without significantly effecting the synthesis.

Example 1

Synthesis of Ribozymes Containing 2'-O-amino Nucleotides

The method of synthesis used follows the procedure for normal RNA synthesis as described in Usman et al., *J. Am. Chem. Soc.* 1987, 109, 7845–7854; Scaringe et al., *Nucleic Acids Res.* 1990, 18, 5433–5441 and Wincott et al., 1995 *Nucleic Acids Res.* 23, 2677–2684 and makes use of common nucleic acid protecting and coupling groups, such as dimethoxytrityl at the 5'-end, and phosphoramidites at the 3'-end (compounds 4, 9, 13, 17, 22, 23). The average stepwise coupling yields were >98%. These base-modified nucleotides may be incorporated not only into hammerhead ribozymes, but also into hairpin, VS ribozymes, hepatitis delta virus, or Group I or Group II introns. They are, therefore, of general use as replacement motifs in any nucleic acid structure.

Example 2

Synthesis of 2'-O-amino pyrimidine nucleoside (8 in FIG. 6)

Synthetic methods for preparing 5'-O—NH$_2$ or 3'-O—NH$_2$ derivatives of 2'-deoxynucleosides by Mitsunobu inversion are well known in the art. However, applicants attempts to apply this method to the preparation of 2'-O—NH$_2$-ribonucleosides resulted in very low yields (<10%) of desired compounds. Applicant has developed a new and highly efficient process for the synthesis of 2'-O—NH$_2$-ribonucleosides and their phosphoramidites.

3',5'-(tetraisopropyldisiloxane-1,3-di-yl)-1-β-D-arabinofuranosyl-pyrimidine (2)

Referring to FIG. 6, 1β-D-arabinofuranosyl-pyrimidine (compound 1), such as 1-β-D-arabinofuranosyl-uracil (2.44 g, 10 mmol) was dried by two co-evaporations with anhydrous pyridine and a re-dissolved in the anhydrous pyridine. The above solution was cooled (0° C.) and a solution of 1,3-dichloro-1,1,3,3-tetraisopropylsiloxane (3.52 mL, 11.0 mmol) in 10 mL of anhydrous dichloroethane was added drop-wise under stirring. The reaction mixture was allowed to warm to room temperature (about 20° C.) and stirred for an additional two hours. The reaction was quenched with MeOH (10 mL) and evaporated to dryness. The residue was dissolved in methylene chloride and washed with saturated NaHCO$_3$ and brine. The organic layer was evaporated to dryness and coevaporated with toluene to remove traces of pyridine to give 4.8 g (98%) of compound 2 which was used without further purification.

2'-O-phthalimido-3',5'-O-(tetraisopropyidisiloxane-1,3-di-yl)-uridine (4)

To the ice-cooled solution of 3',5'-O-(tetraisopropyidisiloxane-1,3-di-yl)-1-β-D-arabinofuranosyl-uracil (4 g, 8.2 mmol) in dichloromethane trifluoromethane sulfonic anhydride (1.66 mL, 9.86 mmol) was added and the reaction mixture was stirred at −5° C. for 30 min. Then it was diluted with dichloromethane and washed with cold 1% aq acetic acid, then with saturated aq sodium bicarbonate and brine. The organic layer was dried over anhydrous sodium sulfate and evaporated to dryness. The resulting derivative 3 was dissolved in anhydrous acetonitrile (70 mL) and N-hydroxyphtalimide (1.74 g, 10.66 mmol) was added. A solution of DBU (diazabicyclo (5.4.0)undec-7-ene) (1.6 mL, 10.66 mmol) in acetonitrile (5 mL) was added dropwise to the reaction mixture under vigorous stirring. After 30 min a dark orange reaction mixture was diluted with dichloromethane (250 mL) and extracted with saturated aq sodium bicarbonate solution (3×250 mL). The resulting colorless organic layer was washed with brine and evaporated to give 3.6 g (70%) of compound 4.

2'-O-phthalimido-uridine (5)

Triethylamine (1.32 mL, 9.5 mmol) and triethylamine trihydrofluoride (1.55 mL, 9.5 mmol) were added simultaneously to the solution of 2'-O-phthalimido-3',5'-O-(tetraisopropyidisiloxane-1,3-di-yl)-uridine (3 g, 4.75 mmol) in dichloromethane. After 1 hour the solvents were removed in vacuo, and remaining residue was dissolved in dichloromethane and evaporated at 35° C. This procedure was repeated 3 times (until Thin Layer Chromatography showed complete conversion of the starting material). The residue was dissolved in dichloromethane and washed with saturated aq sodium bicarbonate and brine. The organic layer was dried over anhydrous sodium sulfate and evaporated to dryness to give 1.56 g (85%) of compound 5.

2'-O-amino uridine (8) was obtained by hydrolysis with 40% aq methylamine and subsequent crystallization from ethanol.

5'-O-dimethoxytrityl-2'-O-phthalimido-utidine (6)

The compound 5 (1.5 g, 4 mmol) was dried by multiple evaporations with anhydrous pyridine, redissolved in dry pyridine, dimethoxytritylchloride (1.2 eq) was added and the reaction mixture was left under anhydrous conditions overnight. Then it was quenched with methanol (15 ml), evaporated, dissolved in chloroform, washed with saturated aq sodium bicarbonate and brine. The organic layer was dried over sodium sulfate and evaporated. The residue was purified by flash chromatography on silica gel eluting with EtOAc-hexanes mixture (2:3) to give 1.93 g (70%) of the corresponding 5'-O-Dimethoxytrityl derivative 6.

5'-O-Dimethoxytrityl-2'-O-phthalimido uridine-3'-(2-Cyanoethyl N,N-diisopropyl) phosphoroamidite (7)

Standard phosphitylation of 6 according to Tuschl et al., Biochemistry 1993, 32, 11658–11668) yielded phosphoramidite 7 in 70% yield.

General Procedure for Phosphitylation: To the ice-cooled stirred solution of protected nucleoside (1 mmol) in dry dichloromethane (20 mL) under argon blanket was added dropwise via syringe the premixed solution of N,N-diisopropylethylamine (2.5 eq) and 2-cyanoethyl N'N-diisopropylchlorophosphoramidite (1.2 eq) in dichloromethane (3 mL). Simultaneously via another syringe N-methylimidazole (1 eq) was added and stirring was continued for 2 hours at room temperature. After that the reaction mixture was again ice-cooled and quenched with 15 ml of dry methanol. After 5 min stirring, the mixture was concentrated in vacuo (<40° C.) and purified by flash chromatography on silica gel using hexanes-ethylacetate mixture contained 1% triethylamine as an eluent to give corresponding phosphoramidite as white foam.

Phosphoramidites were incorporated into nucleic acid molecules, such as ribozymes and substrates, using the method of synthesis, deprotection, purification and testing previously described (Wincott et al., 1995 supra). The average stepwise coupling yields were ~98%.

Example 3

Synthesis of 2'-O-phthalimido-3',5'-O-(tetraisopropyidisiloxane-1,3-di-yl)-N$^6$-t-butylbenzoyl adenosine (5 in FIG. 7) and 2'-O-amino adenosine nucleoside (9 in FIG. 7)

Referring to FIG. 7, 9-β-D-arabinofuranosyl adenine (12 mmol) was silylated with 1,3-dichloro-1,1,3,3-tetraisopropylsiloxane (4.2 mL, 13.2 mmol) as described for the ara-uridine derivative. The cold solution (−10° C.) of the product in anhydrous dichloromethane was treated with trifluoromethanesulfochloride (1.53 mL, 14.4 mmol) for 20 min. The resulting solution was diluted with anhydrous dichloromethane and washed with cold (0° C.) 1% aq acetic acid, then saturated aq NaHCO$_3$ and brine. The organic layer was dried over sodium sulfate and evaporated to dryness to give derivative 2. The residue was dissolved in anhydrous acetonitrile and N-hydroxyphthalimide (2.54 g, 15.6 mmol) was added. A solution of DBU (2.33 mL 15.6 mmol) in anhydrous acetonitrile was added to the resulting reaction mixture under vigorous stirring. After 30 min a dark orange-brown reaction mixture was worked-up as described for uridine derivative. The resulting 2'-O-phthalimido derivative 4 was dissolved in anhydrous pyridine, 4-tert-butylbenzoyl chloride was added and the reaction mixture was left overnight at room temperature. After that it was quenched with methanol (15 mL), solvents were removed in vacuo and the residue dissolved in toluene and evaporated to dryness. The resulting oil was dissolved in dichloromethane, washed with saturated aq NaHCO$_3$ and brine, dried over sodium sulfate and evaporated to dryness. The residue was purified by flash chromatography on silica, using EtOAc-Hexanes (1:2) mixture as an eluent to give 3.5 g (35% on ara-A) of the fully protected synthon 5.

2'-O-phthalimido-N$^6$-t-butylbenzoyl adenosine (6)

Markiewicz-group deprotection was performed analogously to the corresponding uridine derivative. Yield 86%.

2'-O-amino adenosine (9) was obtained by hydrolysis with 40% aq methylamine and subsequent crystallization from ethanol.

5'-O-Dimethoxytrityl-2'-O-phthalimido-N$^6$-t-butylbenzoyl adenosine (7)

Standard dimethoxytritylation of 2'-O-phthalimido-N$^6$-t-butylbenzoyl adenosine afforded compound 7 with 75% yield.

5'-O-Dimethoxytrityl-2'-O-phthalimido-N$^6$-t-butylbenzoyl adenosine 3'-(2-Cyanoethyl N,N-diisopropyl) phosphoroamidite (8)

Standard phosphitylation of according Tuschl et al., supra yielded phosphoramidite 8 in 70% yield.

Example 4

Synthesis of 2'-O-phthalimido-3',5'-O-(tetraisopropyldisiloxane-1,3-di-yl)-N$^6$-t-butylbenzoyl Guanosine (11 in FIG. 8) and 2'-O-amino Guanosine nucleoside (8 in FIG. 8)

Referring to FIG. 8, compound 4 is synthesized starting from compound 1, using the process described in Hansske et al., 1984, Tetrahedron 40, 125, *incorporated by reference herein*. Compounds 8 and 9 can then be synthesized from compound 4 using the procedures described in FIG. 7 and above.

Example 5

RNA cleavage reaction catalyzed by ribozymes substituted with 2'-O-amino modifications RNA cleavage assay in vitro:

Substrate RNA is 5' end-labeled using [γ-$^{32}$P] ATP and T4 polynucleotide kinase (US Biochemicals). Cleavage reactions are carried out under ribozyme "excess" conditions. Trace amount (≦1 nM) of 5' end-labeled substrate and 40 nM unlabeled ribozyme are denatured and renatured separately by heating to 90° C. for 2 min and snap-cooling on ice for 10–15 min. The ribozyme and substrate are incubated, separately, at 37° C. for 10 min in a buffer containing 50 mM Tris-HCl and 10 mM $MgCl_2$. The reaction is initiated by mixing the ribozyme and substrate solutions and incubating at 37° C. Aliquots of 5 μl are taken at regular intervals of time and the reaction is quenched by mixing with equal volume of 2X formamide stop mix. The samples are resolved on 20% denaturing polyacrylamide gels. The results are quantified and percentage of target RNA cleaved is plotted as a function of time.

Referring to FIG. 9A, hammerhead ribozymes with 2'-O-amino-substitutions at position 4, 7, 9 or 15.1 were synthesized as described above. These ribozymes were assayed for their ability to cleave target RNA. As shown in FIG. 9B, all the ribozymes shown in FIG. 9A were capable of catalyzing cleavage of target RNA.

Applications

Various ligands can be attached to oligonucleotides using the compounds of Formula I and/or Formula II for the purposes of cellular delivery, nuclease resistance, cellular trafficking and localization, chemical ligation of oligonucleotide fragments. Incorporation of one or more compounds of Formula I into a ribozyme may increase its effectiveness. Compounds of Formula I can be used as potential antiviral agents.

Diagnostic uses

Ribozymes of this invention may be used as diagnostic tools to examine genetic drift and mutations within diseased cells or to detect the presence of a specific RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE 1

Characteristics of naturally occurring ribozymes

Group I Introns

- Size: ~150 to >1000 nudeotides.
- Requires a U in the target sequence immediately 5' of the deavage site.
- Binds 4–6 nucleotides at the 5'-side of the deavage site.
- Reaction mechanism: attack by the 3'-OH of guanosine to generate deavage products with 3'-OH and 5'-guanosme.
- Additional protein cofactors required in some cases to help folding and maintainance of the active structure [1].
- Over 300 known members of this dass. Found as an intervening sequence in *Tetrahymena thermophila* rRNA, fungal mitochondria, chloroplasts, phage T4, blue-green algae, and others.
- Major structural features largely established through phylogenetic comparisons, mutagenesis, and biochemical studies [2,3].
- Complete kinetic framework established for one ribozyme [4,5,6,7].
- Studies of ribozyme folding and substrate docking underway [8,9,10].
- Chemical modification investigation of important residues well established [11,12].
- The small (4–6 nt) binding site may make this ribozyme too non-specitic for targeted RNA deavage, however, the Tetrahymena group I intron has been used to repair a "defeccive" β-galactosidase message by the ligation of new β-galactosidase sequences onto the defective message [13].

TABLE 1-continued

Characteristics of naturally occurring ribozymes

RNAse P RNA (M1 RNA)

- Size: ~290 to 400 nucleotides.
- RNA portion of a ubiquitous ribonucleoprotein enzyme.
- Cleaves tRNA precursors to form mature tRNA [14[9 .
- Reaction mechanism: possible attack by $M^{2+}$—H to generate cleavage products with 3'-OH and 5'-phosphate.
- RNAse P is found throughout the prokaryotes and eukaryotes. The RNA subunit has been sequenced from bacteria, yeast, rodents, and primates.
- Recruitment of endogenous RNAse P for therapeutic applications is possible through hybridization of an External Cuide Sequence (ECS) to the target RNA [15,16]
- Important phosphate and 2' OH contacts recently identified [17,18]

Group II Introns

- Size: >1000 nucleotides.
- Trans cleavage of target RNAs recently demonstrated [19,20].
- Sequence requirements not fully determined.
- Reaction mechanism: 2'-H of an internal adenosine generates cleavage products with 3'-OH and a "lariat" RNA containing a 3'-5' and a 2'-5' branch point.
- Only natural ribozyme with demonstrated participation in DNA cleavage [21,22] in addition to RNA cleavage and ligation.
- Major structural features largely established through phylogenetic comparisons [23].
- Important 2' OH contacts beginning to be identified [24]
- Kinetic framework under development [25]

Neurospora VS RNA

- Size: ~144 nucleotides.
- Trans cleavage of hairpin target RNAs recently demonstrated [26].
- Sequence requirements not fully determined.
- Reaction mechanism: attack by 2'-OH 5' to the scissile bond to generate cleavage products with 2',3'-cyclic phosphate and 5'-OH ends.
- Binding sites and structural requirements not fully determined.
- Only 1 known member of this class. Found in Neurospora VS RNA.

Hammerhead Ribozyme
(see text for references)

- Size: ~13 to 40 nucleotides.
- Requires the target sequence UH immediately 5' of the cleavage site.
- Binds a variable number nucleotides on both sides of the cleavage site.
- Reaction mechanism: attack by 2'-OH 5' to the scissile bond to generate cleavage products with 2',3'-cyclic phosphate and 5'-OH ends.
- 14 known members of this class. Found in a number of plant pathogens (virusoids) that use RNA as the infectious agent.
- Essential structural features largely defined, including 2 crystal structures []
- Minimal ligation activity demonstrated (for engineering through in vitro selection) []
- Complete kinetic framework established for two or more ribozymes [].
- Chemical modification investigation of important residues well established [].

Hairpin Ribozyme

- Size: ~50 nucleotides.
- Requires the target sequence GUC immediately 3' of the cleavage site.
- Binds 4–6 nucleotides at the 5'-side of the cleavage site and a variable number to the 3'-side of the cleavage site.
- Reaction mechanism: attack by 2'-OH 5' to the scissile bond to generate cleavage products with 2',3'-cyclic phosphate and 5'-OH ends.
- 3 known members of this class. Found in three plant pathogen (satellite RNAs of the tobacco ringspot virus, arabis mosaic virus and chicory yellow mottle virus) which uses RNA as the infectious agent.
- Essential structural features largely defined [27,28,29,30]
- Ligation activity (in addition to cleavage activity) makes ribozyme amenable to engineering through in vitra selection [31]
- Complete kinetic framework established for one ribozyme [32].
- Chemical modification investigation of important residues begun [33,34].

Hepatitis Delta Virus (HDV) Ribozyme

- Size: ~60 nucleotides.
- Trans cleavage of target RNAs demonstrated [35].
- Binding sites.and structural requirements not fully determined, although no sequences 5' of cleavage site are required. Folded ribozyme contains a pseudoknot structure [36].
- Reaction mechanism: attack by 2'-OH 5' to the scissile bond to generate cleavage products with 2',3'-cyclic phosphate and 5'-OH ends.
- Only 2 known members of this class. Found in human HDV.
- Circular form of HDV is active and shows increased nuclease stability [37]

1. Mohr, G.; Caprara, M.G.; Guo, Q.; Lambowitz, A.M. Nature, 370, 147–150 (1994).
2. Michel, Francois; Westhof, Eric. Slippery substrates. Nat. Struct Biol. (1994), 1(1), 5–7.

TABLE 1-continued

Characteristics of naturally occurring ribozymes

3. Lisacek, Frederique; Diaz, Yolande; Michel, Francois. Automatic identification of group I intron cores in genomic DNA sequences. J. Mol. Biol. (1994), 235(4), 1206–17.
4. Herschlag, Daniel; Cech, Thomas R., Catalysis of RNA cleavage by the Tetrahymena thermophila ribozyme. 1. Kinetic description of the reaction of an RNA substrate complementary to the active site. Biochemistry (1990), 29(44), 10159–71.
5. Herschiag, Daniel; Cech, Thomas R., Catalysis of RNA cleavage by the Tetrahymena thermophila ribozyme. 2. Kinetic description of the reaction of an RNA substrate that forms a mismatch at the active site. Biochemistry (1990), 29(44), 10172–80.
6. Knitt, Deborah S.; Herschlag, Daniel. pH Dependencies of the Tetrahymena Ribozyme Reveal an Unconventional Origin of an Apparent pKa. Biochemistry (1996), 35(5), 1560–70.
7. Bevilacqua, Philip C.; Sugimoto, Naoki; Tumer, Douglas H.. A mechanistic framework for the second step of splicing catalyzed by the Tetrahymena ribozyme. Biochemistry (1996), 35(2), 648–58.
8. Li, Yi; Bevilacqua, Philip C.; Mathews, David; Tumer, Douglas H.. Thermodynamic and activation parameters for binding of a pyrene-labeled substrate by the Tetrahyxriena ribozyme: docking is not diffusion-controlled and is driven by a favorable entropy change. Biochemistry (1995), 34(44), 14394–9.
9. Banerjee, Aloke Raj; Tumer, Douglas H.. The time dependence of chemical modification reveals slow steps in the folding of a group I ribozyme. Biochemistry (1995), 34(19), 6504–12.
10. Zarrinkar, Patrick P.; Williamson, James R., The P9.1–P9.2 peripheral extension helps guide folding of the Tetrahymena ribozyme. Nudeic Acids Res. (1996), 24(5), 854–8.
11. Strobel, Scott A.; Cech, Thomas R., Minor groove recognition of the conserved G.cntdot.U pair at the Tetrahymena ribozyme reaction site. Science (Washington, D. C.) (1995), 267 (5198), 675–9.
12. Strobel, Scott A.; Cech, Thomas R., Exocyclic Amine of the Conserved G.cntdot.U Pair at the Cleavage Site of the Tetrahymena Ribozyme Contributes to 5'-Splice Site Selection and Transition State Stabilization. Biochemistry (1996), 35(4), 1201–11.
13. Sullenger, Bruce A.; Cech, Thomas R., Ribozyme-mediated repair of defective mRNA by targeted trans-splicing. Nature (London) (1994), 371(6498), 619–22.
14. Robertson, H.D.; Altman, S.; Smith, J.D. J. BioL Chem., 247 5243–5251 (1972).
15. Forster, Anthony C.; Altman, Sidney. External guide sequences for an RNA enzyme. Science (Washington, D.C., 1883-) (1990), 249(4970), 783–6.
16. Yuan, Y.; Hwang, E. S.; Altman, S. Targeted cleavage of mRNA by human RNase P. Proc. Natl. Acad. Sci. USA (1992) 89, 8006–10.
17. Harris, Michael E.; Pace, Norman R.. Identification of phosphates involved in catalysis by the ribozyme RNase P RNA. RNA (1995), 1(2), 210–18.
18. Pan, Tao; Loria, Andrew; zhong, Kun. Probing of tertiary interactions in RNA: 2'-hydroxyl-base contacts between the RNase P RNA and pr#tRNA. Proc. Natl. Acad. Sci. U. S. A. (1995), 92(26), 12510–14.
19. Pyle, Anna Marie; Green, Justin B.. Building a Kinetic Framework for Group II Intron Ribozyme Activity: Cuantitation of Interdomain Binding and Reaction Rate. Biochemistry (1994), 33(9), 2716–25.
20. Michels, Wmiam J. Jr.; Pyle, Anna Marie. Conversion of a Group II Intron into a New Multiple-Turnover Ribozyme that Selectively Cleaves Oligonucleotides: Elucidation of Reaction Mechanism and Structure/Function Relationships. Biochemistry (1995), 34(9), 2965–77.
21. Zimmerly, Steven; Guo, Huatao; Eskes, Robert; Yang, Jian; Perlman, Philip S.; Lambowitz, Alan M.. A group II intron RNA is a catalytic component of a DNA endonudease involved in intron mobility. Cell (Cambridge, Mass.) (1995), 83(4), 529–38.
22. Griffin, Edmund A., Jr.; Qin, Zhifeng; Michels, Wmiams J., Jr.; Pyle, Anna Marie. Group II intron ribozymes that cleave DNA and RNA linkages with similar efficiency, and lack contacts with substrate 2'-hydroxyl groups. Chem. Biol. (1995), 2(11), 761–70.
23. Michel, Francois; Ferat, Jean Luc. Structure and activities of group II introns. Annu. Rev. Biochem. (1995), 64, 435–61.
24. Abramovitz, Dana L.; Friedman, Richard A.; Pyle, Anna Marie. Catalytic role of 2'-hydroxyl groups within a group II intron active site. Science (Washington, D.C.) (1996), 271(5254), 1410–13.
25. Daniels, Danette L.; Michels, Wimam J., Jr.; Pyle, Anna Marie. Two competing pathways for self-splicing by group fl iritrons: a quantitative analysis of in vitro reaction rates and products. J. Mol. Biol. (1996), 256(1), 31–49.
26. Guo, Hans C. T.; Coliins, Richard A.. Efficient trans-cleavage of a stem-loop RNA substrate by a ribozyme derived ftom Neurospora VS RNA. EMBO J. (1995), 14(2), 368–76.
27. Hampel, Amold; Tritz, Richard; Hicks, Margaret; Cruz, Phillip. 'Hairpin' catalytic RNA model: evidence for helixes and sequence requirement for substrate RNA. Nudeic Adds Res. (1990), 18(2), 299–304.
28. Chowrira, Bharat M.; Berzai-Herranz, Aifredo; Burke, John M.. Novel guanosine requirement for catalysis by the hairpin ribozyme. Nature (London) (1991), 354(6351), 320–2.
29. Berzal-Herranz, Aifredo; Joseph, Simpson; Chowrira, Bharat M.; Butcher, Samuei E.; Burke, John M.. Essential nucleotide sequences and secondary structure elements of the harrpin ribozyme. EMBO J. (1993), 12(6), 2567–73.
30. Joseph, Simpson; Berzal-Herranz, Alfredo; Chowrira, Bharat M.; Butcher, Samuel E.. Substrate seiection rules for the hairpin ribozyme determined by in vitro selection, mutation, and analysis of mismatched substrates. Genes Dev. (1993), 7(1), 130–8.
31. Berzal-Herranz, Alfredo; Joseph, Simpson; Burke, John M. In vitro selection of active hairpin ribozymes by sequentiai RNA#ataiyzed cleavage and ligation reactions. Genes Dev. (1992), 6(1), 129–34.
32. Hegg, Lisa A.; Fedor, Martha J.. Kinetics and Thermodynamics of Intermolecular Catalysis by Hairpin Ribozymes. Biochemistry (1995), 34(48), 15813–28.
33. Grasby, Jane A.; Mersmann, Karin; Singh, Mohinder; Gait, Michaei J.. Purine Functionai Groups in Essential Residues of the Hairpin Ribozyme Required for Cataiytic Cleavage of RNA. Biochemistry (1995), 34(12), 4068–76.

TABLE 1-continued

Characteristics of naturally occurring ribozymes

34. Schimidt, Sabine; Beigelman, Leonid; Karpeisky, Alexander; Usman, Nassim; Sorensen, Uirik S.; Gait, Michael J.. Base and sugar requirements for RNA cleavage of essentiai nucleoside residues in internal loop B of the hairpin ribozyme: implications for secondary structure. Nucleic Acids Res. (1996), 24(4), 573–81.
35. Perrotta, Anne T.; Been, Michael D.. Cleavage of oligoribonudeotides by a ribozyme derived from the hepatitis .delta. virus RNA sequence. Biochemistry (1992), 31(1), 16–21.
36. Perrotta, Anne T.; Been, Michael D.. A pseudoknot-like structure required for efficient self-cleavage of hepatitis delta virus RNA. Nature (London) (1991), 350(6317), 434–6.
37. Puttaraju, M.; Perrotta, Anne T.; Been, Michael D.. A circular trans-acting hepatitis delta virus ribozyme. Nudeic Acids Res. (1993), 21(18), 4253–8.

TABLE 2

2.5 μmol RNA Synthesis Cycle

| Reagent | Equivalents | Amount | Wait Time* |
|---|---|---|---|
| Phosphoramidites | 6.5 | 163 μL | 2.5 |
| S-Ethyl Tetrazole | 23.8 | 238 μL | 2.5 |
| Acetic Anhydride | 100 | 233 μL | 5 sec |
| N-Methyl Imidazole | 186 | 233 μL | 5 sec |
| TCA | 83.2 | 1.73 mL | 21 sec |
| Iodine | 8.0 | 1.18 mL | 45 sec |
| Acetonitrile | NA | 6.67 mL | NA |

*Wait time does not include contact time during delivery.

What is claimed is:

1. A nucleoside or a nucleotide comprising a sugar portion, wherein the 2' position of said sugar has the formula: 2'-O—$NHR_1$, wherein $R_1$ is selected from a group consisting of H, aminoacyl group, peptidyl group, biotinyl group, cholesteryl group, lipoic acid residue, retinoic acid residue, folic acid residue, ascorbic acid residue, nicotinic acid residue, 6-aminopenicillanic acid residue, 7-aminocephalosporanic acid residue, alkyl, alkenyl, alkynyl, aryl, alkylaryl, carbocyclic aryl, heterocyclic aryl, amide and ester.

2. A nucleoside or a nucleotide comprising a sugar portion, wherein the 2' position of said sugar has the formula: 2'-O—N=$R_3$, wherein $R_3$ is selected from a group consisting of pyridoxal residue, pyridoxal-5-phosphate residue, 13-cis-retinal residue, 9-cis-retinal residue, alkyl, alkenyl, alkynyl, alkylaryl, carbocyclic alkylaryl, and heterocyclic alkylaryl.

3. A compound having the formula 1:

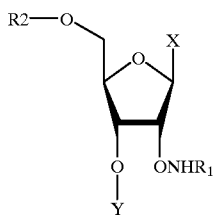

wherein, $R_1$ is selected from a group consisting of H, aminoacyl group, peptidyl group, biotinyl group, cholesteryl group, lipoic acid residue, retinoic acid residue, folic acid residue, ascorbic acid residue, nicotinic acid residue, alkyl, alkenyl, alkynyl, aryl, alkyaryl, carbocyclic aryl, heterocyclic aryl, amide and ester;

X is independently a nucleotide base or its analog or hydrogen;

Y is independently a phosphorus-containing group; and

R2 is independently a blocking group or a phosphorus-containing group.

4. A compound having the formula II:

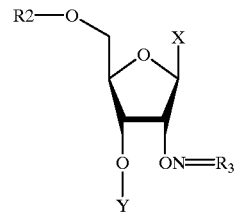

wherein, $R_3$ is selected from a group consisting of pyridoxal residue, pyridoxal-5-phosphate residue, 13-cis-retinal residue, 9-cis-retinal residue, alkyl, alkenyl, alkynyl, alkylaryl, carbocyclic alkylaryl, and heterocyclic alkylaryl;

X is independently a nucleotide base or its analog or hydrogen;

Y is independently a phosphorus-containing group; and

R2 is independently a blocking group or a phosphorus-containing group.

5. The compound of claim 1 or claim 2, wherein said compound is a nucleotide.

6. The compound of claim 1 or claim 2, wherein said compound is a nucleotide-tri-phosphate.

7. The compound of claim 1, wherein said compound is 2'-O-amino adenosine.

8. The compound of claim 1, wherein said compound is 2'-O-amino guanosine.

9. The compound of claim 1, wherein said compound is 2'-O-amino cytidine.

10. The compound of claim 1, wherein said compound is 2'-O-amino uridine.

11. A pharmaceutical composition comprising a compound of claim 1 or claim 2.

12. A process for the synthesis of a 2'-O-amino nucleoside comprising the steps of:

a) contacting a 3' and 5'-protected arabino nucleoside with sulfonylating reagent under conditions suitable for the formation of 3' and 5'-protected 2'-arabino sulfonyl nucleoside;

b) displacing the sulfonyl group from said 2'-arabino sulfonyl nucleoside with N-hydroxy-phthalimide in the presence of a strong organic base under conditions suitable for the formation of 3' and 5'-protected 2'-O-N-phthaloyl ribonucleoside;

c) deprotecting said phthaloyl ribonucleoside with a fluoride containing reagent under conditions suitable for the formation of 2'-O-N-phthaloyl ribonucleoside; and d) contacting said 2'-O-N-phthaloyl ribonucleoside with a reagent selected from a group consisting of alkylamine, hydrazine, N-phenyl hydrazine and N-alkylhydrazine, under conditions suitable for the formation of said 2'-O-amino nucleoside.

13. The process of claim 12, wherein said sulfonylating reagent is tri-fluoromethane sulfonic anhydride.

14. The process of claim 12, wherein said sulfonylating reagent is tri-fluoromethane sulfonic chloride.

15. The process of claim 12, wherein said strong organic base is 1,8-diazabicyclo(5.4.0)undec-7-ene.

16. The process of claim 12, wherein said fluoride containing reagent is selected from a group consisting of tetrabutylammonium fluoride and triethylamine trihydrofluoride.

17. The process of claim 12, wherein said alkylamine is aqueous methylamine.

18. The process of claim 12, wherein said N-alkylhydrazine is N-methylhydrazine.

* * * * *